(12) United States Patent
Prestwich et al.

(10) Patent No.: US 8,722,649 B2
(45) Date of Patent: May 13, 2014

(54) ALPHA-CHLORO AND ALPHA-BROMO PHOSPHONATE ANALOGS OF LYSOPHOSPHATIDIC ACID AND METHODS OF MAKING AND USING THEREOF

(75) Inventors: Glenn Prestwich, Eastbound, WA (US); Gabor Tigyi, Memphis, TN (US); Guowei Jiang, Springfield, NJ (US); Guanghui Yang, Shanghai (CN); Joanna Gajewiak, Salt Lake City, UT (US); Honglu Zhang, Guilderland, NY (US); Xiaoyu Xu, Salt Lake City, UT (US)

(73) Assignees: University of Utah Research Foundation, Salt Lake City, UT (US); University of Tennessee Research Foundation, Knoxville, TN (US)

( * ) Notice: Subject to any disclaimer, the term of this patent is extended or adjusted under 35 U.S.C. 154(b) by 878 days.

(21) Appl. No.: 12/664,543

(22) PCT Filed: Jun. 13, 2008

(86) PCT No.: PCT/US2008/066934
§ 371 (c)(1),
(2), (4) Date: Jun. 10, 2010

(87) PCT Pub. No.: WO2008/157361
PCT Pub. Date: Dec. 24, 2008

(65) Prior Publication Data
US 2010/0261681 A1  Oct. 14, 2010

Related U.S. Application Data

(60) Provisional application No. 60/944,120, filed on Jun. 15, 2007.

(51) Int. Cl.
*A61K 31/661* (2006.01)
*C07F 9/10* (2006.01)

(52) U.S. Cl.
USPC .......................................... 514/120; 558/179

(58) Field of Classification Search
USPC .......................................... 514/120; 558/179
See application file for complete search history.

(56) References Cited

U.S. PATENT DOCUMENTS

| 2007/0088002 A1 | 4/2007 | Lynch et al. |
| 2007/0123492 A1 | 5/2007 | Prestwich et al. |

FOREIGN PATENT DOCUMENTS

WO    2004092188    10/2004

OTHER PUBLICATIONS

Grant & Hackh's Chemical Dictionary (5th Ed. 1987) at p. 148.*
Deng et al., "The Lysophosphatidic Acid Type 2 Receptor Is Required for Protection Against Radiation-Induced Intestinal Injury," Gastroenterology 2007; 132:1834-1851.
International Search Report and combination Written Opinion mailed Sep. 8, 2008 in re PCT/US08/66934, filed Jun. 13, 2008.
Jaing et al., "α-Substituted Phosphonate Analogues of Lysophosphatidic Acid (LPA) Selectively Inhibit Production and Action of LPA," ChemMedChem 2007, 2, 679-690.
Supplementary European Search Report dated May 22, 2012 for European Application No. 08771032.

* cited by examiner

*Primary Examiner* — Samantha Shterengarts
(74) *Attorney, Agent, or Firm* — Gardner, Groff, Greenwald & Villanueva, P.C.

(57) ABSTRACT

Described herein is the synthesis and pharmacology of a series of α-substituted methylene phosphonate analogs, in which the α-$CH_2$ moiety is replaced with CHCl or CHBr.

11 Claims, 15 Drawing Sheets

(a), CCl₄, PPh₃, Py.; (b), CBr₄, PPh₃, toluene, 60%; (c), *p*-TsOH, CH₃OH, 81%; (d), RCOCl, 2,4,6-collidine, CH₂Cl₂, -78°C; (e), TMSBr, CH₂Cl₂; CH₃OH/H₂O; (f), Dowex ion-exchange.

a b

Untreated

*anti* isomer 1b

A

B

A          B

C

D

ALPHA-CHLORO AND ALPHA-BROMO PHOSPHONATE ANALOGS OF LYSOPHOSPHATIDIC ACID AND METHODS OF MAKING AND USING THEREOF

CROSS REFERENCE TO RELATED APPLICATIONS

This application claims priority upon U.S. provisional application Ser. No. 60/944,120, filed Jun. 15, 2007. This application is hereby incorporated by reference in its entirety for all of its teachings.

ACKNOWLEDGEMENTS

The research leading to this invention was funded in part by the National Institutes of Health, Grant Nos. HL070231, NS29632, CA921160, and HL61469. The U.S. Government has certain rights in this invention.

BACKGROUND

Lysophosphatidic acid (LPA, 1-radyl-sn-glycerol-3-phosphate) elicits growth factor-like effects in almost every cell type. At the organ system level, LPA is implicated in complex physiological responses that include immunological competence, brain development, wound healing, coagulation, and regulation of blood pressure. The pleiotropic physiological functions of LPA suggest that LPA could contribute to a number of pathophysiological states including cancer, atherosclerosis, hypertension, ischemia reperfusion injury, diabetes, cardiovascular diseases, stroke, prevention of toxicity of chemotherapy and radiation therapy, immunomodulation and others.

LPA can be produced either extracellularly or intracellularly in response to various stimuli including growth factors, LPA itself, phorbol esters, and epidermal growth factor (EGF). In the course of blood coagulation, LPA is mainly generated sequentially by two enzymatic reactions. First, the action of phospholipase $A_1$ and $A_2$ (PLA) on phosphatidylcholine (PC) yields lysophosphatidylcholine (LPC). Second, the lysophospholipase D (lysoPLD) activity of autotaxin (ATX) converts LPC to LPA. ATX is one of the forty most upregulated genes in invasive cancers, and has been implicated in cell motility and tumor invasion, metastasis, and neovascularization. LPA signals through the activation of specific receptors which in turn leads to distinct cellular events depending in the receptor subtype expressed by the targeted cell. Cell surface LPA receptors belong to the membrane G protein-coupled receptors (GPCR) protein family. There are five different LPA GPCR characterized on the surface of mammalian cells: $LPA_1$, $LPA_2$, $LPA_3$, $LPA_4$ and $LPA_5$. The first three were formerly called endothelial differentiation genes (EDG), EDG2, EDG4, EDG 7, whereas GPR23/P2Y9 and GPR92, tentatively designated as $LPA_4$ and $LPA_5$ respectively, are members of the purinergic cluster in the GPCR superfamily. Cancer cells of different cellular origins express LPA GPCR subtypes in $LPA_1$ in differing amounts; however, $LPA_1$ is the most widely expressed in almost every cancer cell type, whereas, $LPA_4$ seems to be expressed at very low levels. Ovarian and breast cancer cells express multiple isoforms of the LPA GPCRs and LPA accumulates in tumor cell ascites and in tumor cell effusates. LPA also activates the nuclear transcription factor peroxisome proliferator-activated receptor γ (PPARγ). Through activation of these GPCRs and PPARγ, LPA regulates multiple physiological and pathological responses.

The involvement of LPA receptors in many pathophysiologies have implicated them as attractive targets for therapeutic intervention. As with many other GPCRs; LPA receptors should be amenable to the development of highly specific and potent agonists or antagonists that have favorable pharmacokinetic, bioavailability, and metabolic characteristics. Currently available compounds represent a promising but limited start to the development of useful chemical tools, although none can be considered definitive in determining receptor selectivity or biological functions, especially for studies in vivo. The development of more selective, more stable, more potent, and more drug-like agonists and antagonists is eagerly awaited, and has been a bottleneck in therapeutic exploration.

SUMMARY

Described herein is the synthesis and pharmacology of a series of α-substituted methylene phosphonate analogs, in which the $CH_2$ moiety is replaced with CHCl or CHBr. The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

LPA analog mixed diastereomers 1 (10 mg/kg) or separate diastereomers 1a or 1b (3 mg/kg) reduces tumor size in an orthotopic breast cancer xenograft model. At 6 weeks, 1a and 1b were statistically different from controls (p<0.01)

Figure 10:
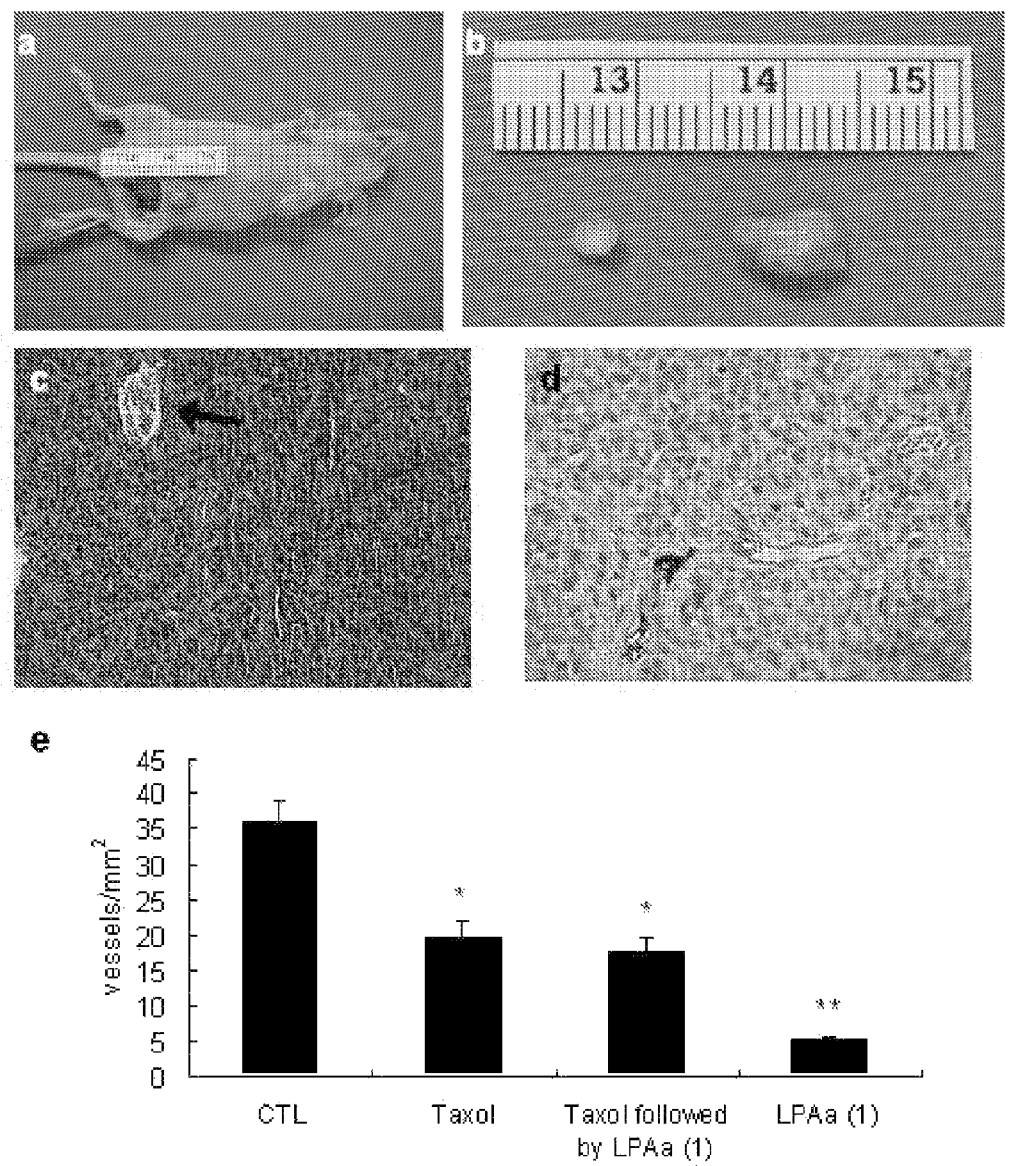

FIG. 10 shows α-bromo LPA analog 1 treatment decreases tumor size and vascularity in an orthotopic breast cancer xenograft model. Gross view of breast cancers in the control group (panel a) at the end of the experiments, which used subcutaneous injection of MDA-MB-231 cells suspended in Extracel™. Panel b: Difference in gross tumor size after removal. The H&E staining (panel c) and immunohistochemical staining with CD31 specific endothelial markers (panel d) of the control group tissue samples show relative angiogenesis within the cancer cells. Panel e: Newly generated vessels in the tumor samples were quantified in six different fields of three slides for each treatment group. Asterisks indicate that the Taxol treatment and Taxol treatment (*) followed by BrP-LPA 1 was statistically different from the control (p<0.05) but not different from each other. Treatment with BrP-LPA 1 alone had lower blood vessel density (**) than the controls (p<0.001) or either of the Taxol treatments (p<0.05).

Figure 11:
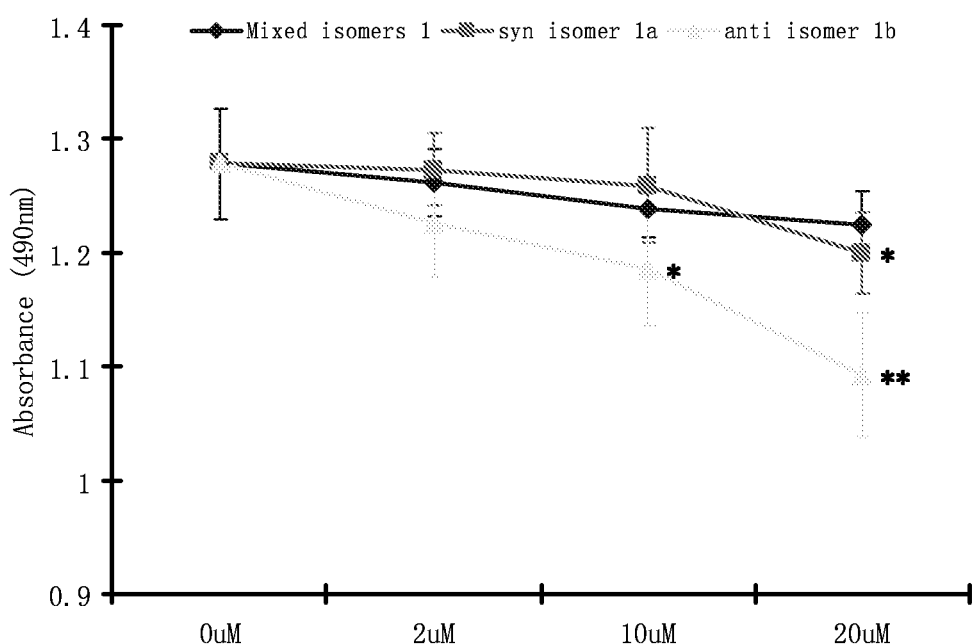

FIG. 11 shows the effect of α-bromo LPA analogs as LPA receptor pan-Antagonists on HCT 116 cell proliferation. (* p<0.05, ** p<0.01).

Figure 12:
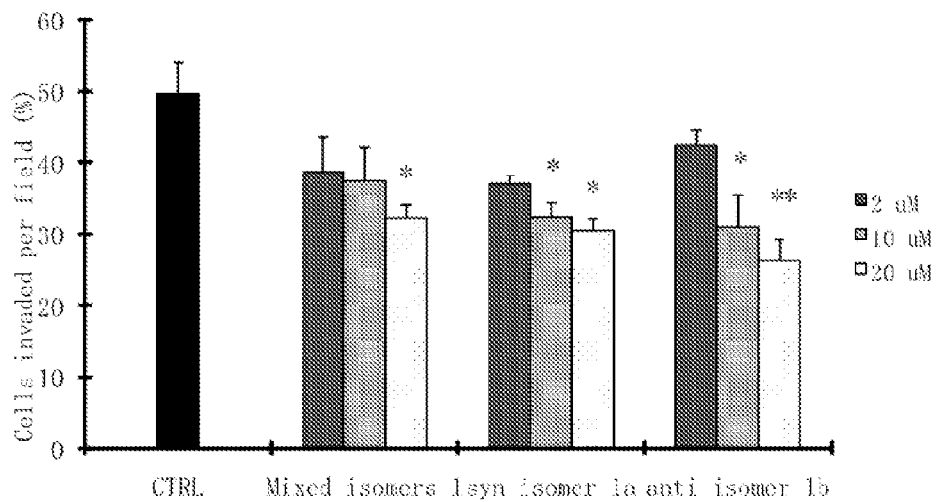

FIG. 12 shows the effect of α-bromo LPA analogs 1a and 1b as LPA receptor pan-Antagonists on HCT cell invasion (* p<0.05, ** p<0.01).

Figure 13:
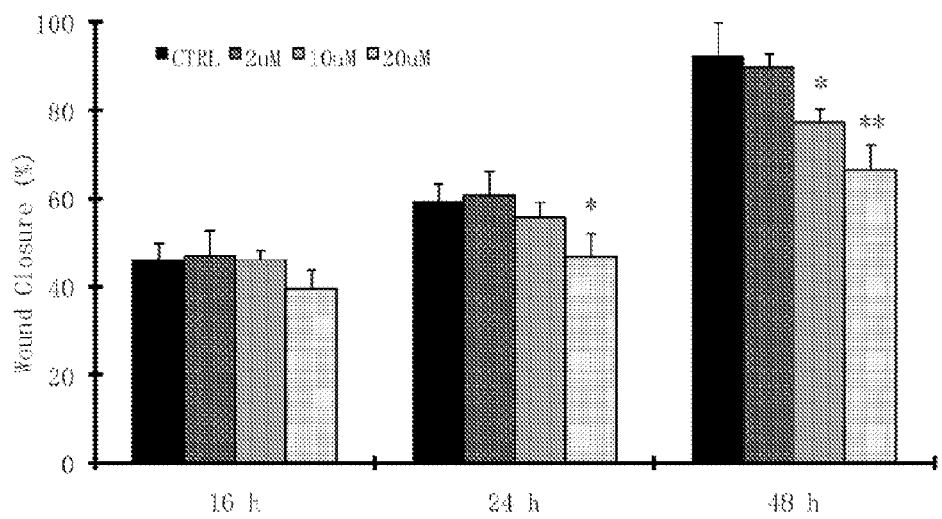

FIG. 13 shows the effect of the α-bromo LPA analog 1b as a LPA receptor pan-antagonists on HCT cell migration (* p<0.05, ** p<0.01).

Figure 14:
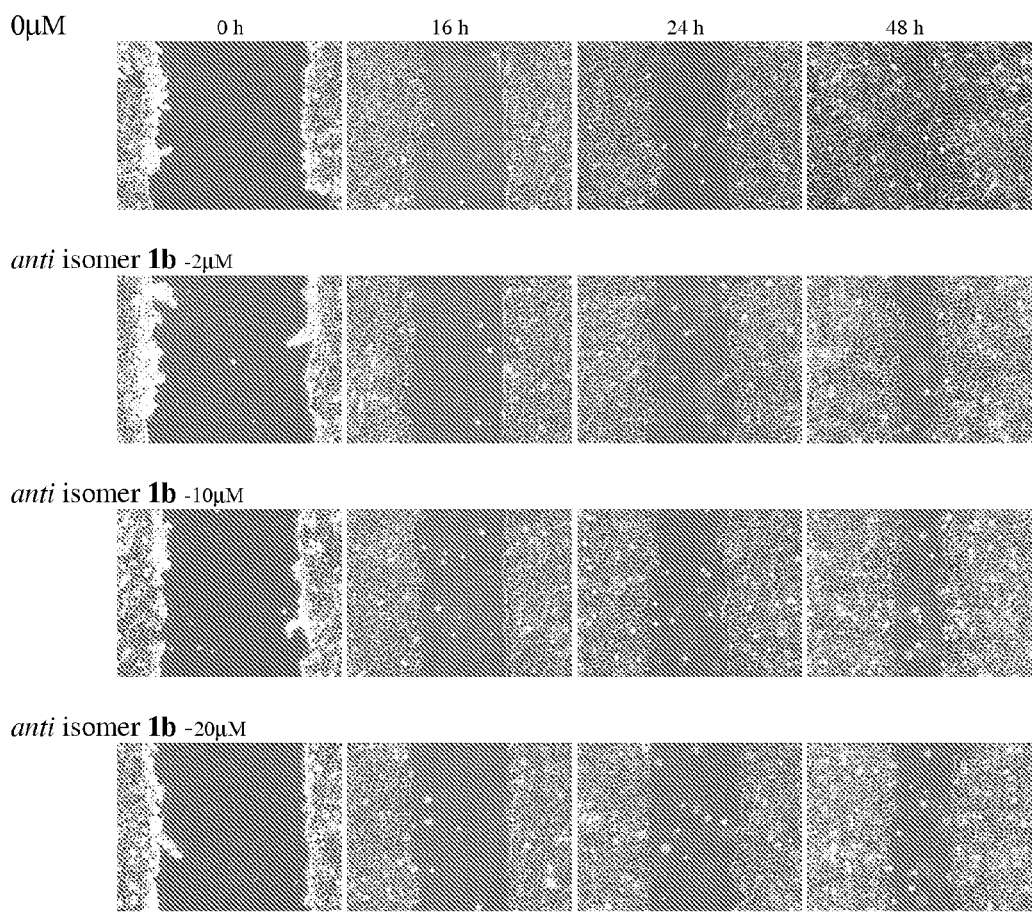

FIG. 14 shows photographs of the effect of the α-bromo LPA analog 1b as a LPA receptor pan-Antagonists on HCT cell migration. HCT 116 cells were treated with anti isomer 1b followed by assessment of cell migration at various time point using wound-healing assay.

Figure 15:
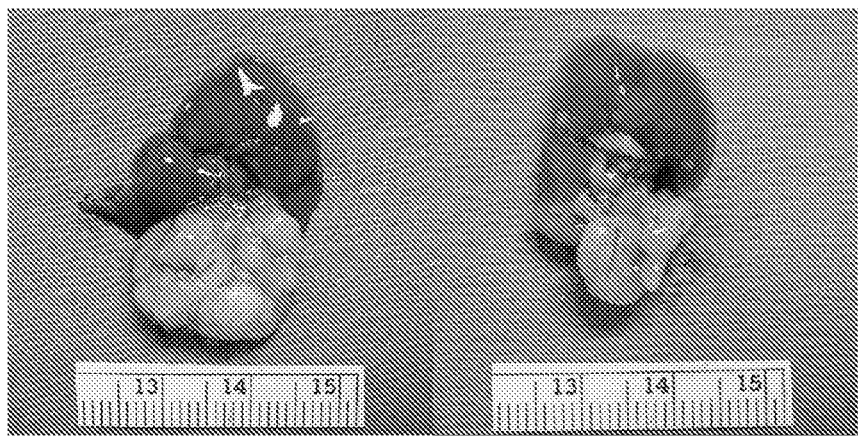
Figure 15:
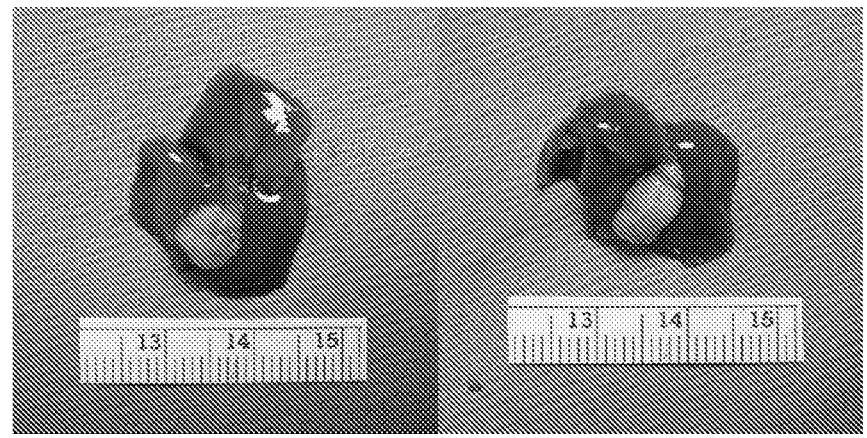

FIG. 15 shows the effect of the α-bromo LPA analog 1b on hepatic colon cancer growth. Representative images of excised livers are shown for each group. All nude mice in both group developed liver tumors. The tumor in anti isomer 1b treatment group was smaller than the untreated control.

Figure 16:
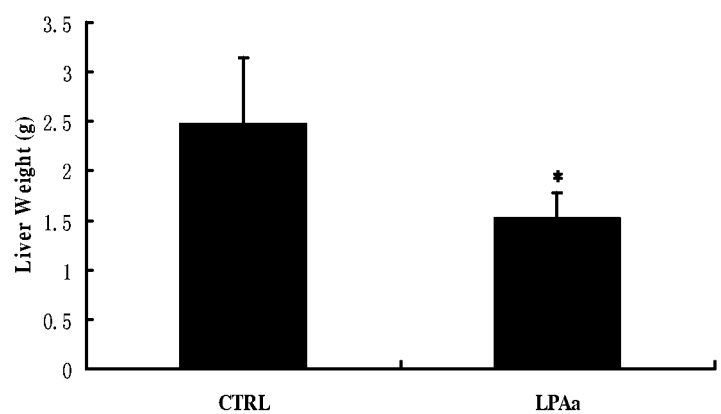
Figure 16:
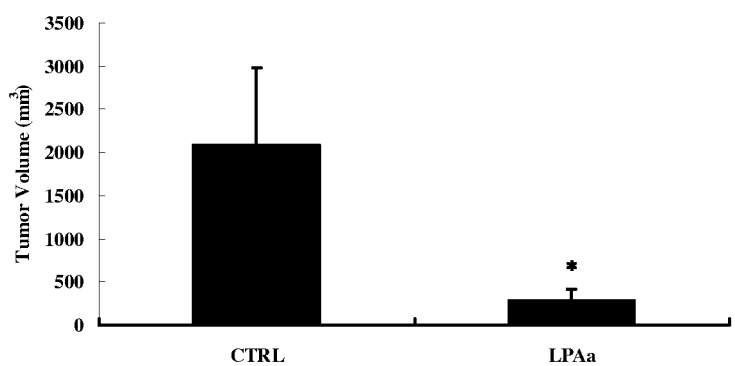

FIG. 16 shows the effect of anti isomer 1b on hepatic tumor growth. HCT 116 colon cancer cells were injected directly into the liver of nude mice to form hepatic tumors. After 3 weeks of tumor growth, livers were excised and liver weight and tumor diameters were determined. A. Anti isomer 1b significantly reduced tumor burden (* p<0.05, Student's t test); B. Tumor volume of anti isomer 1b treated group were significantly smaller than untreated group (* p<0.05, Student's t test).

Figure 17:
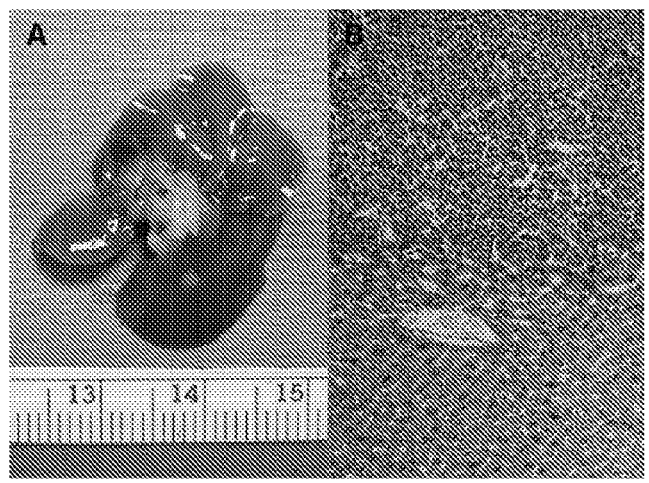
Figure 17:
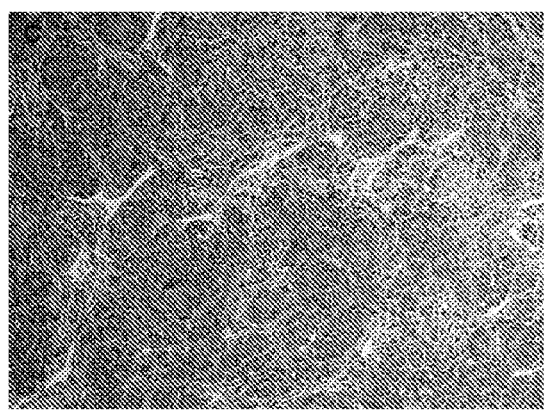
Figure 17:
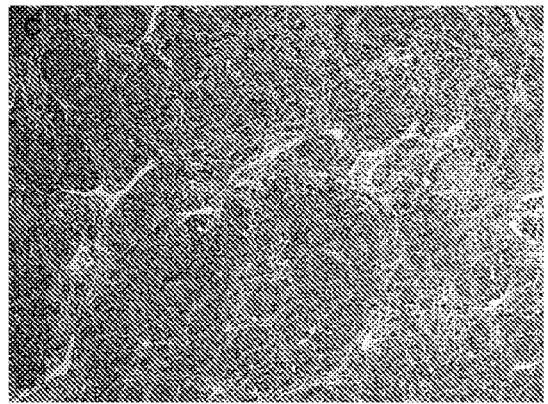

FIG. 17. (A) Shows the liver of a nude mouse involved with colon tumor. (B) Pathohistology of tumor-involved nude mouse liver as shown in A. The upper section shows hepatic colon cancer growth on nude mouse. The lower section shows the native nude mouse liver (100×). (C, D) H&E staining of a hepatic colon cancer, where C is untreated and D includes LPAa 1b treatment (100×).

DETAILED DESCRIPTION

Before the present compounds, compositions, articles, devices, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not. For example, the phrase "optionally substituted lower alkyl" means that the lower alkyl group can or can not be substituted and that the description includes both unsubstituted lower alkyl and lower alkyl where there is substitution.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

Variables such as $R^1$, $R^2$, $R^3$, $R^6$, $R^7$, $X^1$, $X^2$, $X^3$, $Y^1$, $Y^2$, U, V, and W used throughout the application are the same variables as previously defined unless stated to the contrary.

The term "substantially" with respect to the stereochemistry at carbons a and b refers to greater than 95%, greater than 97%, greater than 98%, greater than 99%, greater than 99.5%, or 100% of one enantiomer with respect to the other enantiomer. The terms "R" and "S" with respect to the stereochemistry at carbon a are also referred to in the art as "D" and "L," respectively. The term "substantially" as defined above also applies to diastereoisomers, where a compound can be a substantially pure diastereoisomer.

The term "alkyl group" as used herein is a branched or unbranched saturated hydrocarbon group of 1 to 25 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. Examples of longer chain alkyl groups include, but are not limited to, an oleate group or a palmitate group. A "lower alkyl" group is an alkyl group containing from one to six carbon atoms.

The term "cycloalkyl group" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom such as, but not limited to, nitrogen, oxygen, sulphur, or phosphorus.

The term "aryl group" as used herein is any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

The term "silyl group" as used herein is represented by the formula —SiRR'R", where R, R', and R" can be, independently, hydrogen, an alkyl, aryl, cycloalkyl, halogenated alkyl, alkoxy, or heterocycloalkyl group described above.

The term "protecting group" as used herein is a group that can be chemically bound to an oxygen atom, and subsequently removed (either chemically, in-vitro, or in-vivo) from the oxygen atom by predictable methods. Examples of many of the possible protective groups can be found in *Protective Groups in Organic Synthesis* by T. W. Green, John Wiley and Sons, 1981, which is incorporated herein by reference in its entirety.

I. α-Chloro and α-Bromo Analogs of LPA

In one aspect described herein are compounds having the formula I

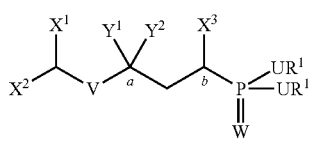

wherein $X^1$, $X^2$, $Y^1$, and $Y^2$ comprises, independently, hydrogen, fluorine, a hydroxyl group, a branched or straight chain $C_1$ to $C_{25}$ alkyl group, $OR^2$, $OCH_2CH_2OR^2$, $OC(O)R^3$, or $NC(O)R^3$;

each U comprises, independently, oxygen, sulfur, or $NR^1$;

V is not present or when V is present, V comprises oxygen or sulfur;

W comprises oxygen or sulfur;

$X^3$ is chlorine or bromine;

each $R^1$ comprises, independently, hydrogen, a branched or straight chain $C_1$ to $C_{25}$ alkyl group, a cationic counterion, or both $R^1$ form a cyclic or heterocyclic group;

$R^2$ comprises hydrogen, a branched or straight chain $C_1$ to $C_{25}$ alkyl group, a cycloalkyl group, a heterocycloalkyl group, an aryl group, a heteroaryl group or a protecting group;

$R^3$ comprises a branched or straight chain $C_1$ to C25 alkyl group, a cycloalkyl group, a heterocycloalkyl group, an aryl group, a heteroaryl group, or the pharmaceutically acceptable salt or ester thereof, wherein when $Y^1$ and $Y^2$ are different groups, the stereochemistry at carbon a is either substantially R or substantially S, and the compound is a single diastereoisomer or a mixture of diastereoisomers.

The compounds having the formula I are α-Cl or α-Br analogs of LPA. In one aspect, each U comprises oxygen, W is oxygen, V is not present, $X^1$ is hydrogen, $X^2$ is hydroxy, and $X^3$ is chloro. In another aspect, each U comprises oxygen, W is oxygen, V is not present, $X^1$ is hydrogen, $X^2$ is hydroxy, $X^3$ is chloro, $Y^1$ is hydrogen, $Y^2$ is $OC(O)R^3$, wherein $R^3$ is a branched or straight chain $C_1$ to $C_{25}$ alkyl group, and $R^1$ is hydrogen. In another aspect, each U comprises oxygen, W is oxygen, V is not present, $X^1$ is hydrogen, $X^2$ is hydroxy, $X^3$ is chloro, $Y^1$ is hydrogen, $Y^2$ is $OC(O)R^3$, wherein $R^3$ is an oleate group or a palmitate group, $R^1$ is hydrogen, and the stereochemistry at carbon a is substantially R or S.

In another aspect, each U comprises oxygen, W is oxygen, V is not present, $X^1$ is hydrogen, $X^2$ is hydroxy, and $X^3$ is bromo. In another aspect, each U comprises oxygen, W is oxygen, V is not present, $X^1$ is hydrogen, $X^2$ is hydroxy, $X^3$ is bromo, $Y^1$ is hydrogen, $Y^2$ is $OC(O)R^3$, wherein $R^3$ is a branched or straight chain $C_1$ to $C_{25}$ alkyl group, and $R^1$ is hydrogen. In another aspect, each U comprises oxygen, W is oxygen, V is not present, $X^1$ is hydrogen, $X^2$ is hydroxy, $X^3$ is bromo, $Y^1$ is hydrogen, $Y^2$ is $OC(O)R^3$, wherein $R^3$ is an oleate group or a palmitate group, $R^1$ is hydrogen, and the stereochemistry at carbon a is substantially R or S. In another aspect, the compound having the formula I is

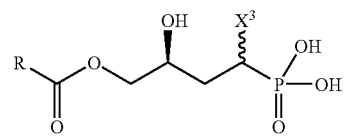

wherein R is $C_{17}H_{33}$ or $C_{15}H_{31}$ and $X^3$ is Cl or Br, or the pharmaceutically-acceptable salt or ester thereof.

The compounds having the formula I can be a substantially pure diastereoisomer or can exist as a mixture of diastereoisomers. In the case when carbons a and h are chiral centers, four possible diastereoisomers are possible. For example, when the stereochemistry at carbon a is substantially R, the stereochemistry at carbon b is either substantially R or S. Alternatively, when the stereochemistry at carbon a is substantially S, the stereochemistry at carbon b is either substantially R or S. Using the techniques described herein, it is possible to synthesize single diastereoisomers. In one aspect, the compound having the formula I is

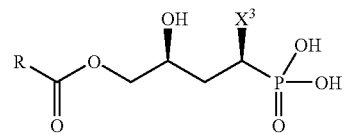

-continued

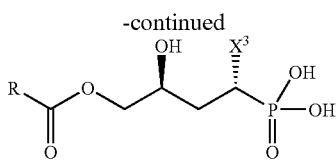

wherein R is $C_{17}H_{33}$ or $C_{15}H_{31}$ and $X^3$ is Cl or Br, or the pharmaceutically-acceptable salt or ester thereof. Separate enantiomers or separate diastereomers of a given chemical structure can be prepared to control toxicology and receptor pharmacology.

Any of the compounds described herein can be the pharmaceutically acceptable salt or ester thereof. Pharmaceutically acceptable salts are prepared by treating the free acid with an appropriate amount of a pharmaceutically acceptable base. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. In one aspect, the reaction is conducted in water, alone or in combination with an inert, water-miscible organic solvent, at a temperature of from about 0° C. to about 100° C. such as at room temperature. The molar ratio of compounds of structural formula I to base used are chosen to provide the ratio desired for any particular salts. For preparing, for example, the ammonium salts of the free acid starting material, the starting material can be treated with approximately one equivalent of pharmaceutically acceptable base to yield a neutral salt.

Ester derivatives are typically prepared as precursors to the acid form of the compounds—as illustrated in the examples below—and accordingly can serve as prodrugs. Generally, these derivatives will be lower alkyl esters such as methyl, ethyl, and the like. Amide derivatives —(CO)NH$_2$, —(CO)NHR and —(CO)NR$_2$, where R is an alkyl group defined above, can be prepared by reaction of the carboxylic acid-containing compound with ammonia or a substituted amine.

II. Methods for Preparing α-Chloro and α-Bromo LPA Analogs

Figure 1:
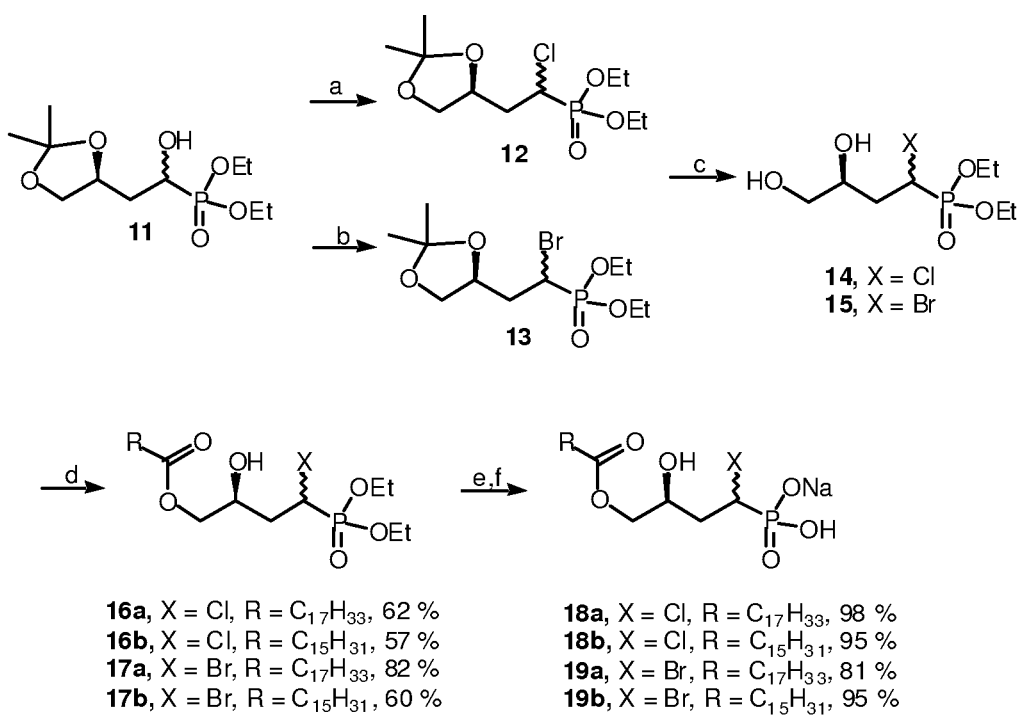
FIG. 1 shows the synthesis of the diastereoisomeric mixture of α-chloro and α-bromomethylene phosphonate analogs of LPA.
Figure 2:
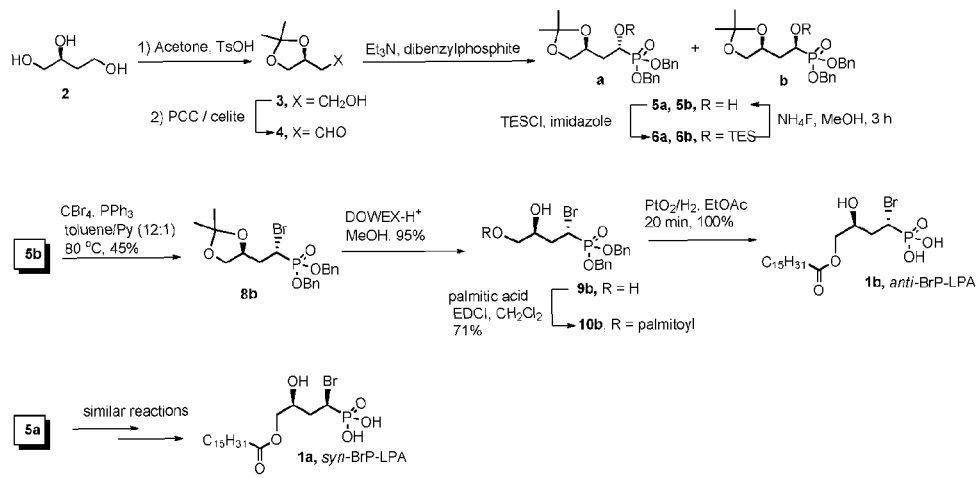
FIG. 2 shows the synthesis of syn- and anti-BrP-LPA isomers 1a and 1b.
Figure 3:
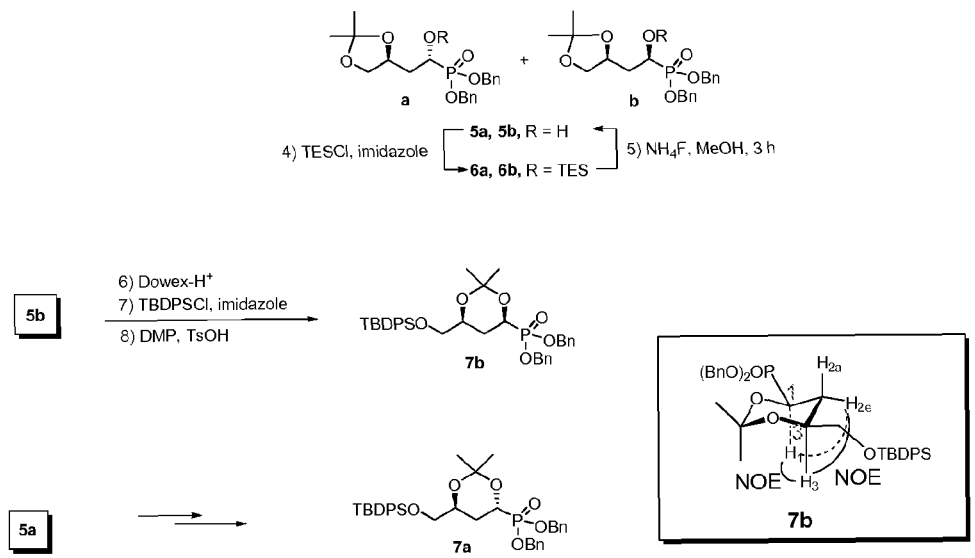
FIG. 3 shows the formation of a cyclic intermediate to establish the configuration at the alpha carbon.
Figure 4:
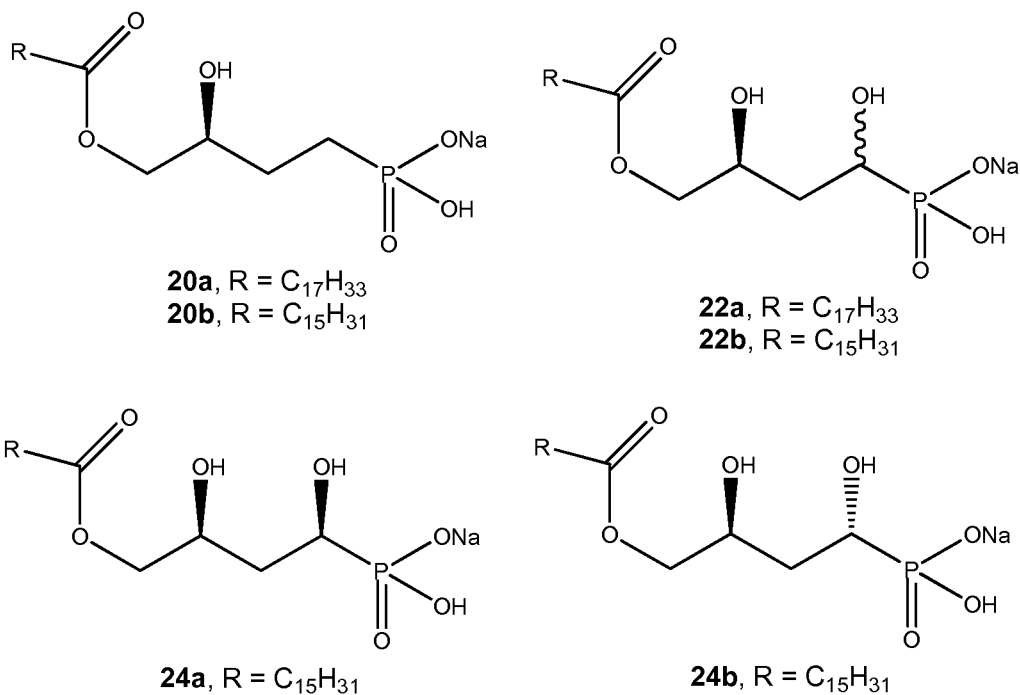
FIG. 4 shows the structure of methylene phosphonate analogs and α-hydroxy methylene phosphonate analogs evaluated and compared to a-bromo methylene phosphonate analogs described herein.

In one aspect, described herein are methods for preparing compounds having the formula I. FIGS. 1-3 show several reaction schemes for producing α-chloro and α-bromo analogs of LPA. The reactions generally involve converting a α-hydroxyl group to the corresponding α-chloro or α-bromo compound. For example, the compounds having the formula II

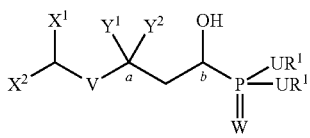

where each variable is defined as above, can be reacted with $CCl_4$ or $CBr_4$ in the presence of $PPh_3$ to convert the hydroxyl group at carbon b to a chloro or bromo group, respectively. Specific procedures for producing the α-chloro and α-bromo compounds are provided in the Examples below. Depending upon the selection of starting materials, various groups can be protected with protecting groups so that the a-hydroxyl group at carbon b can be converted to the α-chloro group or α-bromo group. Depending on the method selected and the a-hydroxy diastereomer used, different degrees of diastereo-selectivity, i.e., the ratio of the two diastereomers produced, can be obtained.

The methods described herein can produce single diastereoisomers or mixtures of diastereoisomers. FIG. 1 depicts an exemplary procedure for making diastereomeric mixtures of the a-chloro and α-bromo compounds. A single diastereomer is defined herein as one with greater that 50% diastereomeric excess (de), i.e., a ratio of diastereoisomers of 2:1. In most cases, de values of greater than 80% are preferred. FIG. 2 shows an exemplary method of obtaining the separate α-hydroxy diastereomers and FIG. 3 illustrates the method of determining the absolute stereochemistry of an αhydroxy diastereomer using NMR of a cyclic derivative. In one aspect, mixtures of diastereoisomers can be converted to single diastereoisomers, which is depicted in FIG. 2 and in the Examples.

III. Pharmaceutical Compositions

In one aspect, any of the compounds having the formula I can be combined with at least one pharmaceutically-acceptable carrier to produce a pharmaceutical composition. The pharmaceutical compositions can be prepared using techniques known in the art. In one aspect, the composition is prepared by admixing the compound having the formula I with a pharmaceutically-acceptable carrier. The term "admixing" is defined as mixing the two components together so that there is no chemical reaction or physical interaction. The term "admixing" also includes the chemical reaction or physical interaction between the compound having the formula I and the pharmaceutically-acceptable carrier.

Pharmaceutically-acceptable carriers are known to those skilled in the art. These most typically would be standard carriers for administration to humans, including solutions such as sterile water, saline, and buffered solutions at physiological pH.

Molecules intended for pharmaceutical delivery may be formulated in a pharmaceutical composition. Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally).

Preparations for administration include sterile aqueous or non-aqueous solutions, suspensions, and emulsions. Examples of non-aqueous carriers include water, alcoholic/aqueous solutions, emulsions or suspensions, including saline and buffered media. Parenteral vehicles, if needed for collateral use of the disclosed compositions and methods, include sodium chloride solution, Ringer's dextrose, dextrose and sodium chloride, lactated Ringer's, or fixed oils. Intravenous vehicles, if needed for collateral use of the disclosed compositions and methods, include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

It will be appreciated that the actual preferred amounts of active compound in a specified case will vary according to the specific compound being utilized, the particular compositions formulated, the mode of application, and the particular situs and mammal being treated. Dosages for a given host can be determined using conventional considerations, e.g. by customary comparison of the differential activities of the subject compounds and of a known agent, e.g., by means of an appropriate conventional pharmacological protocol. Physicians and formulators, skilled in the art of determining doses of pharmaceutical compounds, will have no problems determining dose according to standard recommendations (Physicians Desk Reference, Barnhart Publishing (1999).

IV. Methods of Use

LPA is associated with a number of different pathophysiological states. Reducing the production of LPA is a plausible approach to reducing or preventing undesirable states attributed to LPA activity. As discussed above, LPA is mainly generated sequentially by two enzymatic reactions. First, the action of phospholipase $A_1$ and $A_2$ (PLA) on phosphatidylcholine (PC) yields lysophosphatidylcholine (LPC). Second, the lysophospholipase D (lysoPLD) activity of autotaxin (ATX) converts LPC to LPA. In one aspect, the compounds and compositions described herein inhibit autotaxin (ATX). The term "inhibit" as defined herein is the ability of the compounds or compositions described herein to reduce a desired feature or prevent an increase of the feature versus a control (e.g., in the absence of any treatment with the compounds or compositions described herein). For example, the phrase "inhibiting ATX activity" includes reducing ATX activity versus a control as well as maintaining ATX activity at the same level or relatively same level prior to administration of the compound or composition. As shown in the Examples below, the compounds described herein are potent ATX inhibitors. By inhibiting ATX activity, LPA production is reduced, which corresponds to the prevention or reduction of certain diseases and undesirable conditions.

In another aspect, the compounds and compositions described herein are antagonist of a LPA GPCR receptor. LPA signals through the activation of specific receptors, which in turn leads to distinct cellular events depending in the receptor subtype expressed by the targeted cell. For example, LPA receptor mediated activation of the Rho and Rac GTPase pathways are essential for the regulation of the actin cytoskeleton and cell motility, which is associated with enhanced tumor cell invasion and metestasis. Cell surface LPA receptors belong to the membrane G protein-coupled receptors (GPCR) protein family. There are five different LPA GPCRs characterized on the surface of mammalian cells: $LPA_1$, $LPA_2$, $LPA_3$, $LPA_4$ and $LPA_5$. In one aspect, the compounds described herein are antagonist of $LPA_4$. As shown in the Examples below, the compounds described herein are effective antagonist of $LPA_4$ GPCR, which has not been demonstrated until now.

The compounds have numerous therapeutic applications due to their ability to inhibit ATX activity and behave as an antagonist for LPA receptors. The compounds described herein can be used to treat or prevent in a subject a number of diseases associated with LPA including, but not limited to, cancer, atherosclerosis, hypertension, ischemia reperfusion injury, diabetes, cardiovascular diseases, stroke, prevention of toxicity of chemotherapy and radiation therapy, or immunomodulation.

In one aspect, the compounds can be used to prevent or treat a metastatic form of cancer. The local production of LPA by ATX/lysoPLD could support the invasion of tumor cells, promoting metastasis. As discussed above, the mechanism of enhanced tumor cell invasion by LPA includes two important molecular mechanisms. ((1) LPA receptor mediated activation of the Rho and Rac GTPase and (2) upregulation of ATX). Thus, the compounds described herein have potential anticancer activity due to their ability to inhibit ATX activity and behave as LPA receptor antagonists. Examples of different types of cancer that can be treated or prevented include, but are not limited to, breast cancer, liver cancer, stomach cancer, colon cancer, pancreatic cancer, ovarian cancer, lung cancer, kidney cancer, prostate cancer, testicular cancer, glioblastoma, sarcoma, bone cancer, head-and-neck cancers, and skin cancer.

As shown in the Examples below, the compounds described herein are effective in anti-cancer treatment. In one aspect, the compounds and compositions described herein can inhibit the ability of cancer cells to invade a biological matrix such as, for example, the extracellular matrix (ECM). The matrix of interest can be contacted with one or more compounds or compositions described herein in vivo or ex vivo to inhibit cancer cell invasion. The ability of cancer cells to invade biological matrices such as the ECM has been linked to a number of different forms of cancer.

In another aspect, the compounds and compositions described herein can inhibit the migration of cancer cells into uninfected tissues of a subject. The ability of cancer cells to migrate to healthy tissues is one mechanism for spreading cancer within a subject. The cancer cells can be contacted with the compounds or compositions described herein using techniques known in the art to inhibit the migration of the cancer cells (see the Examples below).

In one aspect, the compounds and compositions described herein can inhibit cancer cell proliferation. For example, the contacting the cancer cells with the compounds and compositions described herein can reduce or prevent growth of the cancer cells (see the Examples below).

In another aspect, described herein are methods for inhibiting tumor angiogenesis. One approach to cancer therapy is to reduce the number or density of blood vessels that feed the tumor. The compounds and compositions described herein can reduce or prevent blood vessel formation in a tumor, which can ultimately lead to the death of cancer cells and reduction of the tumor (see the Examples below). The method generally involves contacting the tumor with a compound or composition described herein using techniques known in the art.

Based on the different mechanisms by which the compounds and compositions described herein can interact with cancer cells, the compounds and compositions are effective in cancer therapy. In particular, the compounds and compositions are effective in reducing or maintaining the size of a tumor (see the Examples below), which is very important in cancer therapy.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

I. Preparation and Characterization of Diastereomeric Mixtures (FIG. 1)

General. Chemicals were purchased and used without prior purification. Solvents were reagent-grade and distilled before use. $CH_2Cl_2$ was distilled from $CaH_2$ and THF was distilled from sodium wire. TLC used pre-coated silica gel aluminum sheets. Flash chromatography (FC) employed Whatman 230-400 mesh ASTM silica gel. NMR spectra were recorded on a Varian INOVA 400 at 400 MHz ($^1H$), 101 MHz ($^{13}C$), 162 MHz ($^{31}P$) and 376 MHz ($^{19}F$) at 25° C. Chemical shifts are reported in ppm with TMS as internal standard (δ=0.00); $^{31}P$, 85% $H_3PO_4$ (δ=0.00); $^{19}F$, $CFCl_3$ (δ=0.00). Reaction schemes for producing the compounds are provided in FIGS. 1-9.

1-Diethylphosphonyl-1-chloro-3,4-O-isopropylidene-1(R,S)-3(S),4-butanetriol (12). Pyridine (1 mL) was added in one portion to a mixture of diethyl 1-hydroxyalkyphosphonate 11 (1.35 g, 4.77 mmol) and triphenylphosphine (1.53 g, 5.73 mmol) in $CCl_4$ (12 mL). After the mixture was refluxed for 15 h, the solvent is removed in vacuo, and the crude was extracted with EtOAc and hexane mixture (7/3, v/v). The organic phase was filtered through a 1 in. bed of Celite 521 and the solvent was evaporated under reduced pressure. Silica gel flash chromatography. (EtOAc /hexane,2/3, v/v) gave 12 as a colorless oil (960 mg, 71%): $R_f$ 0.55 (EtOAc); $^1H$ NMR ($CDCl_3$) δ 4.30 (m, 1H), 4.15 (m, 4H), 4.05 (m, 1.5H), 3.85 (m, 0.5H), 3.55 (m, 1H), 2.25 (m, 1.50H), 1.85 (m, 0.50H), 1.25-1.37 (m, 12H); $^{13}C$ NMR ($CDCl_3$) δ 109.2 (d, J=14.1 Hz), 73.8 (s), 72.7 (d, J=14.1 Hz), 68.7 (d, J=18.2 Hz), 63.6 (dd, J=42.4 Hz, 7.1 Hz), 37.5 (dd, J=36.4 Hz, 20.8 Hz), 27.1 (s), 26.9 (s), 25.5 (s), 16.3 (s); $^{31}P$ NMR ($CDCl_3$) δ 21.24 (s), 20.64 (s); MS (CI) m/z 300.9 (M$^+$+1). HRMS (CI) for $C_{11}H_{23}ClO_5P$ (M$^+$+1): found 301.0985, calcd 301.0971.

1-Diethylphosphonyl-1-bromo-3,4-O-isopropylidene-1(R,S)-3(S),4-butanetriol (13). Carbon tetrabromide (555 mg, 1.671 mmol) is added in one portion to a stirred solution of diethyl 1-hydroxyalkyphosphonate 11 (480 mg, 1.453 mmol) and triphenylphosphine (476 mg, 1.817 mmol) in dry toluene (2 mL) at 0° C. Stirring is continued for 15 min at this temperature, and then the mixture is refluxed for 9 H. The solvent is removed in vacuo, and the crude was extracted with EtOAc and hexane mixture (7/3, v/v). The organic phase was filtered through a 1 in. bed of Celite 521 and the solvent was evaporated under reduced pressure. Silica gel flash chromatography (EtOAc/hexane, 2/3, v/v) gave 13 as a colorless oil (351 mg, 60%): $R_f$ 0.28 (EtOAc/hexane, 2/1, v/v); $^1H$ NMR ($CDCl_3$) δ 4.33 (m, 1H), 4.15 (m, 4H), 4.05 (m, 2H), 3.55 (m, 1H), 2.25 (m, 1.30H), 1.92 (m, 0.70H), 1.25-1.37 (m, 12H); $^{13}C$ NMR ($CDCl_3$) δ 109.2 (d, J=14.1 Hz), 73.8 (s), 72.7 (d, J=14.1 Hz), 68.7 (d, J=18.2 Hz), 63.6 (dd, J=42.4 Hz, 7.1 Hz), 37.5 (dd, J=36.4 Hz, 20.8 Hz), 27.1 (s), 26.9 (s), 25.5 (s), 16.3 (s); $^{31}P$ NMR ($CDCl_3$) δ 21.02 (s), 20.49 (s); MS (ESI) m/z 345.11, 347.10 (M$^+$+1). HRMS (MALDI) for $C_{11}H_{23}BrO_5P$ (M$^+$+1): found 345.0461, 347.0380, calcd 345.0388, 347.0368.

Diethyl[1-chloro-3(S)-4-dihydroxybutyl]-phosphonate (14). Compound 12 (900 mg, 3.0 mmol) dissolved in 20 mL $CH_3OH$ containing p-toluenesulfonic acid monohydrate (57 mg, 0.1 eq, 0.3 mmol). The mixture was stirred at room temperature for overnight. Next, $NaHCO_3$ (25 mg) was added, and the solvent was evaporated. The residue was purified by silica gel flash chromatography (EtOAc/$CH_3OH$, 10:1, v/v) gave 14 as a colorless oil (750 mg, 96%): $R_f$ 0.23 (EtOAc/$CH_3OH$, 6/1, v/v); $^1H$ NMR ($CDCl_3$) δ 4.12-4.26 (m, 4H), 3.90 (m, 3H), 3.60 (m, 1H), 3.45 (m, 1H), 2.10 (m, 1.50H), 1.75 (m, 0.50H), 1.25-1.37 (m, 6H); $^{13}C$ NMR ($CDCl_3$) δ 68.7 (d, J=8.4 Hz), 67.7 (d, J=13.0 Hz), 66.5 (s), 65.5 (s), 64.3 (dd, J=47.0, 7.7 Hz), 63.5 (s), 60.3 (s), 39.2 (s), 48.6 (dd, J=163.0 Hz, 27.0 Hz), 35.9 (d, J=97.8 Hz), 16.3 (m); $^{31}P$ NMR ($CDCl_3$) δ 22.35 (s), 21.89 (s); MS (CI) m/z 261.0 (M$^+$+1); HRMS (CI) for $C_8H_{19}ClO_5P$ (M$^+$+1): found 261.0656, calcd 261.0659.

Diethyl[1-bromo-3(S)-4-dihydroxybutyl]-phosphonate (15). Compound 13 (80 mg, 0.233 mmol) was dissolved in 1.5 mL $CH_3OH$ containing p-toluenesulfonic acid monohydrate (2.2 mg, 0.05 eq, 0.012 mmol). The mixture was stirred at room temperature for overnight. Next, $NaHCO_3$ (3.6 mg) was added, and the solvent was evaporated. The residue was purified by silica gel flash chromatography (EtOAc/$CH_3OH$, 10/1, v/v) gave 15 as a colorless oil (67 mg, 95%): $R_f$ 0.42 (EtOAc/$CH_3OH$, 6/1, v/v); $^1H$ NMR ($CDCl_3$) δ 4.12-4.26 (m, 4H), 4.00 (m, 0.5H), 3.93 (m, 0.5H), 3.64 (m, 1H), 3.49 (m, 2H), 2.18 (m, 1.30H), 1.85 (m, 0.70H), 1.25-1.37 (m, 6H); $^{13}C$ NMR ($CDCl_3$) δ 69.2 (d, J=40.0 Hz), 66.5 (s), 64.0 (s), 63.7 (s), 39.2 (s), 36.5 (dd, J=106.6 Hz, 64.6 Hz), 16.4 (s); $^{31}P$ NMR ($CDCl_3$) δ 22.07 (s); HRMS (MALDI) for $C_8H_{19}BrO_5P$ (M$^+$+1): found 305.0148, 307.0129, calcd 305.0154, 307.0133.

Diethyl[1-chloro-3(S)-hydroxyl-4-(oleoyloxy)butyl]-phosphonate (16a) was obtained as a colorless oil in 62% yield from precursor 14 after purification by flash chromatography. $R_f$ 0.17 (EtOAc/hexane, 1/1, v/v); $^1H$ NMR ($CDCl_3$) δ 5.30 (m, 2H), 4.00-4.30 (m, 9H), 2.31 (t, J=7.2 Hz, 2H), 2.25 (br, 1.5H), 1.93 (m, 4H), 1.63 (m, 2.5H), 1.16-1.32 (m, 26H), 0.84 (t, J=6.4 Hz, 3H); $^{13}C$ NMR ($CDCl_3$) δ 173.9 (d, J=7.7 Hz), 129.8 (d, J=27.8 Hz), 68.0 (s), 67.2 (s), 66.2 (d, J=6.9 Hz), 65.8 (s), 65.7 (s), 64.7 (d, J=7.0 Hz), 63.6 (m), 37.2 (s), 35.9 (s), 34.1 (d, J=3.0 Hz), 33.9 (s), 29.7 (s), 29.6 (s), 29.5 (s), 29.3 (s), 29.1 (m), 27.1 (m), 25.6 (s), 24.9 (d, J=4.5 Hz), 22.6 (s), 16.4 (m), 14.1. (s); $^{31}P$ NMR ($CDCl_3$) δ 21.98 (s), 21.78 (s); MS (CI) m/z 525.3 (M$^+$+1); HRMS (CI) for $C_{26}H_{51}ClO_6P$ (M$^+$+1): found 525.3105, calcd 525.3112.

Diethyl[1-chloro-3(S)-hydroxyl-4-(palmitoyloxy)butyl]-phosphonate (16b) was obtained in 57% yield from precursor 14. $^1H$ NMR ($CDCl_3$) δ 4.15-4.25 (m, 5H), 4.00-4.15 (m, 3H), 2.32 (t, J=7.8 Hz, 2H), 2.20 (br, 1.4H), 1.90 (m, 0.6H), 1.63 (m, 2H), 1.16-1.32 (m, 30H), 0.85 (t, J=6.8 Hz, 3H); $^{13}C$ NMR ($CDCl_3$) δ 173.9 (s), 68.1 (s), 67.2 (s), 67.0 (m), 64.5 (s), 63.9 (s), 63.4 (s), 37.2 (s), 36.0 (s), 34.1 (s), 31.9 (s), 29.7 (s), 29.6 (m), 29.4 (s), 29.3 (s), 29.2 (s), 29.1 (s), 24.9 (s), 22.7 (s), 16.4 (d, J=6.2 Hz), 14.1 (s); $^{31}P$ NMR ($CDCl_3$) δ 22.02 (s), 21.75 (s); HRMS (CI) for $C_{24}H_{49}ClO_6P$ (M$^+$+1): found 499.2902, calcd 499.2955.

Diethyl[1-bromo-3(S)-hydroxyl-4-(oleoyloxy)butyl]-phosphonate (17a) was obtained as a colorless oil in 82% yield from precursor 15 after purification by flash chromatography. $^1H$ NMR ($CDCl_3$) δ 5.31 (m, 2H), 4.00-4.28 (m, 7.5H), 3.45 (m, 0.5H), 2.31 (t, J=8.0 Hz, 2H), 2.20 (br, 1.4H), 1.93 (m, 4.6H), 1.63 (m, 2H), 1.16-1.32 (m, 26H), 0.84 (t, J=6.4 Hz, 3H); $^{13}C$ NMR ($CDCl_3$) δ 173.9 (d, J=7.8 Hz), 129.9 (d, J=30.8 Hz), 68.0 (s), 67.1 (m), 63.9 (d, J=7.0 Hz), 63.6 (m), 39.0 (s), 36.1 (s), 34.1 (s), 33.9 (s), 31.9 (s), 29.7 (m), 29.5 (s), 29.3 (s), 29.1 (m), 27.1 (m), 25.6 (s), 24.9 (s), 22.6 (s), 16.4 (m), 14.1 (s); $^{31}P$ NMR ($CDCl_3$) 21.93 (s), 21.55 (s); HRMS (MALDI) for $C_{26}H_{50}BrO_6P$ (M+Na$^+$): found 591.2414, 593.2416, calcd 591.2426, 593.2406.

Diethyl[1-bromo-3(S)-hydroxyl-4-(palmitoyloxy)butyl]-phosphonate (17b) was obtained in 60% yield from precursor 15. NMR (CDCl$_3$) δ 4.15-4.25 (m, 4H), 4.00-4.15 (m, 3.5H), 3.45 (m, 0.5H), 2.31 (t, J=8.0 Hz, 2H), 2.20 (br, 1H), 1.90 (m, 1H), 1.63 (m, 2H), 1.16-1.32 (m, 30H), 0.84 (t, J=6.8 Hz, 3H); $^{13}$C NMR (CDCl$_3$) δ 173.9 (d, J=8.5 Hz), 67.9 (s), 67.0 (m), 63.5 (d, J=7.0 Hz), 63.7 (m), 39.0 (s), 37.6 (m), 36.1 (s), 34.1 (s), 33.9 (s), 31.9 (s), 29.6 (m), 29.4 (s), 29.3 (s), 29.2 (s), 29.1 (s), 25.6 (s), 24.9 (s), 22.6 (s), 16.4 (d, J=5.4 Hz), 14.1 (s); $^{31}$P NMR (CDCl$_3$) δ 21.90 (s), 21.56 (s); HRMS (MALDI) for $C_{24}H_{48}BrO_6P$ (M$^+$+1): found 543.2445, 545.2428, calcd 543.2450, 545.2430.

[1-Chloro-3(S)-hydroxyl-4-(oleoyloxy)butyl]-phosphonate (18a) was obtained in 98% yield from precursor 16a. $^1$H NMR (CDCl$_3$/CD$_3$OD) δ 5.24 (m, 2H), 3.90-4.05(m, 4H), 2.25 (t, J=7.8 Hz, 2H), 1.91 (m, 4H), 1.52 (m, 4H), 1.12-1.28 (m, 20H), 0.78 (t, J=6.8 Hz, 3H); $^{13}$C NMR (CDCl$_3$/CD$_3$OD) δ 174.2 (s), 129.8 (d, J=27.0 Hz), 67.8 (s), 67.0 (s), 65.5 (s), 65.4 (s), 36.7 (s), 36.0 (s), 33.9 (s), 33.4 (s), 31.7 (s), 29.1-30.2 (m), 27.0 (s), 24.0 (d, J=3.1 Hz), 25.4 (s), 24.7 (s), 22.5 (s), 13.9 (s); $^{31}$P NMR 8 (CDCl$_3$/CD$_3$OD) 20.68 (s), 20.32 (s); MS (CI) m/z 469.3 (M$^+$+1); HRMS (CI) for $C_{22}H_{43}Cl_6P$ (M$^+$+1): found 469.2456, calcd 469.2486.

[1-Chloro-3(S)-hydroxyl-4-(palmitoyloxy)butyl]-phosphonate (18b) was obtained in 95% yield from precursor 16b. NMR (CDCl$_3$/CD$_3$OD) δ 4.05-4.25 (m, 3H), 2.27 (t, J=7.8 Hz, 2H), 2.10 (br, 1.2H), 1.85 (m, 0.8H), 1.54 (m, 2H), 1.16-1.32 (m, 24H), 0.80 (t, J=6.8 Hz, 3H); $^{13}$C NMR (CDCl$_3$/CD$_3$OD) δ 174.6 (s), 68.2 (s), 67.4 (s), 66.0 (s), 37.1 (s), 36.4 (s), 34.3 (s), 32.1 (s), 29.9 (s), 29.7 (m), 25.0 (s), 22.9 (s), 22.7 (s), 14.3 (s); $^{31}$P NMR (CDCl$_3$/CD$_3$OD) δ 20.75 (s); HRMS (ESI) for $C_{20}H_{41}ClO_6P$ (M$^+$+1): found 443.2326, calcd 443.2329.

[1-Bromo-3(S)-hydroxyl-4-(oleoyloxy)butyl]-phosphonate (19a) was obtained in 81% yield from precursor 17a. $^1$H NMR (CDCl$_3$/CD$_3$OD) δ 5.31 (m, 2H), 4.05-4.21(m, 3.5H), 3.36 (m, 0.5H), 2.34 (t, J=7.8 Hz, 2H), 2.08 (br, 0.8H), 1.97 (m, 5.2H), 1.59 (m, 2H), 1.16-1.32 (m, 20H), 0.85 (t, J=6.8 Hz, 3H); $^{13}$C NMR (CDCl$_3$/CD$_3$OD) δ 174.4 (s), 129.8 (d, J=23.9 Hz), 67.8 (s), 50.9 (s), 34.1 (s), 32.8 (s), 31.9 (s), 29.1-30.2 (m), 27.2 (s), 24.8 (s), 22.7 (s), 14.1 (s); $^{31}$P NMR (CDCl$_3$/CD$_3$ODD) δ 21.57 (s), 21.25 (s); HRMS (MALDI) for $C_{22}H_{42}BrNaO_6P$ (M+Na$^+$): found 535.1803, 537.1813, calcd 535.1800, 537.1779.

[1-Bromo-3(S)-hydroxyl-4-(palmitoyloxy)butyl]-phosphonate (19b) was obtained in 95% yield from precursor 17b. $^1$H NMR (CDCl$_3$/CD$_3$OD) δ 4.05-4.25 (m, 3.5H), 3.70 (br, 0.5H), 2.33 (t, J=7.8 Hz, 2H), 2.20 (br, 1.2H), 2.00 (m, 0.8H), 1.59 (m, 2H), 1.16-1.32 (m, 24H), 0.85 (t, J=6.8 Hz, 3H); $^{13}$C NMR (CDCl$_3$/CD$_3$ODD) δ 174.5 (s), 67.8 (s), 67.0 (s), 50.6 (s), 37.0 (s), 34.1 (s), 32.9 (s), 31.9 (s), 29.7 (s), 29.3 (m), 29.2 (s), 24.8 (s), 22.7 (s), 14.1 (s); $^{31}$P NMR (CDCl$_3$/CD$_3$ODD) δ 22.09 (s), 21.84 (s); HRMS (MALDI) for $C_{20}H_{40}BrNaO_6P$ (M+Na$^+$): found 509.1641, 511.1515, calcd 509.1644, 511.1623.

II. Preparation and Characterization of Single Diastereoisomers (FIGS. 2 and 3)

General synthetic protocols. Chemicals were purchased from Aldrich and Acros Chemical Corp. and used without prior purification. Solvents were reagent-grade and distilled before use: CH$_2$Cl$_2$ was distilled from CaH$_2$, and THF was distilled from sodium wire. TLC used precoated silica gel aluminum sheets (EM Science silica gel 60F$_{254}$). Flash chromatography (FC) employed Whatman 230~400 mesh ASTM silica gel. NMR spectra were recorded on a Varian INOVA 400 at 400 MHz ($^1$H), 101 MHz ($^{13}$C), 162 MHz ($^{31}$P) and 376 MHz ($^{19}$F) at 25° C. Chemical shifts are reported in ppm with TMS as internal standard (□=0.00); $^{31}$P, 85% H$_3$PO$_4$ (□=0.00); $^{19}$F, CFCl$_3$=0.00). Low and high-resolution mass spectra were obtained on HP5971A MSD and Finnigan MAT95 double focusing mass spectrometer (MS) instruments, respectively.

(S)-2,2-Dimethyl-1,3-dioxolane-4-acetaldehyde (4). A solution of triol 2 (25.0 g) and p-TsOH (1.25 g) in acetone (400 mL) was stirred for 3 h at rt. The resulting mixture was neutralized with 20 mL of triethylamine (TEA), concentrated, extracted with EtOAc, and the combined organics dried over Na$_2$SO$_4$ and concentrated to afford acetonide 3. The crude product was dissolved in 800 mL of CH$_2$Cl$_2$ and treated with DCC (150 g) and celite (150 g). After shaking for 2.5 h, the mixture was diluted with 1.5 L of Et$_2$O and filtered. The filtrate was concentrated to a residue, re-dissolved in 200 mL Et$_2$O, and filtered through a short silica gel column to give the crude aldehyde 4 (20 g). This intermediate was not stable and was used directly in the next step without further purification.

Dibenzyl-1-hydroxy-3-(((S)-2,2-dimethyl-1,3-dioxolan-4-yl)-ethylphosphonate (5). A solution of aldehyde 4 obtained above (1.9 g, 13.2 mmol) and dibenzylphosphite (5 mL, 22.5 mmol) was treated with TEA (3.5 mL, 25.6 mmol) at rt. After 18 h, the mixture was concentrated and chromatographed on silica gel (hexanes/EtOAc, 1:1) to give the pure product 5 (4.4 g, 82%) as a colorless oil.

(R)-Dibenzyl-1-O-triethylsilyl-3-((S)-2,2-dimethyl-1,3-dioxolan-4-yl)-ethylphosphonate (6a) and (S)-Dibenzyl-1-O-triethylsilyl-3-((S)-2,2-dimethyl-1,3-dioxolan-4-yl)-ethylphosphonate (6b). A solution of phosphonate 5 (210 mg, 0.52 mmol) and imidazole (408 mg, 6.0 mmol) in CH$_2$Cl$_2$ (5 mL) was treated with TESCl (0.50 mL, 3.0 mmol) at rt. After 12 h the mixture was concentrated and subjected to the aqueous workup. The organic phase was concentrated, and the residue was chromatographed on silica gel (hexanes/EtOAc, 5:1) giving pure product 6a (80 mg, 30%) and 6b (120 mg, 44%) as colorless oil. 6a: $[α]^D_{20}$=−16.6 (c 1.2, CHCl$_3$); $^1$H NMR (400 MHz, CDCl$_3$) δ 7.33-7.32 (m, 10H), 5.08-4.95 (m, 4H), 4.30-4.19 (m, 2H), 4.02 (dd, J=8.0, 6.0 Hz, 1H), 3.49 (t, J=7.2 Hz, 1H), 1.95-1.79 (m, 2H), 1.36 (s, 3H), 1.32 (s, 3H), 0.96 (t, J=7.6 Hz, 9H), 0.68 (qd, J=10.0, 2.0 Hz, 6H); $^{13}$C NMR (101 MHz, CDCl$_3$) δ 136.7, 136.6, 128.8, 128.7, 128.6, 128.58, 128.4, 128.39, 128.2, 109.1, 71.7, 71.6, 69.7, 68.2, 68.1, 67.8, 67.77, 67.6, 65.9, 36.7, 27.3, 25.9, 7.0, 5.0; $^{31}$P NMR (162 MHz, CDCl$_3$) δ 25.71(1P); MALDI-HRMS [M+K]$^+$ calcd for $C_{27}H_{41}O_6$PSiK 559.2042, found 559.2027. 6b: $[α]^D_{20}$=+2.6 (c 1.0, CHCl$_3$); $^1$H NMR (400 MHz, CDCl$_3$) δ 7.24-7.23 (m, 10H), 4.99-4.86 (m, 4H), 4.23 (dt, J=13.2, 6.8 Hz, 1H), 4.05 (q, J=6.8 Hz, 1H), 3.90 (dd, J=8.4, 6.0 Hz, 1H), 3.37 (dd, J=8.0, 6.8 Hz, 1H), 1.97 (t, J=6.8 Hz, 1H), 1.93 (t, J=6.8 Hz, 1H), 1.30 (s, 3H), 1.19 (s, 3H), 0.87 (t, J=7.6 Hz, 9H), 0.68 (qd, J=8.4, 1.2 Hz, 6H); $^{13}$C NMR (101 MHz, CDCl$_3$) δ 136.7, 136.6, 136.56, 136.5, 128.8, 128.7, 128.6, 128.3, 128.2, 108.8, 73.0, 72.9, 69.8, 68.2, 68.1, 68.07, 68.06, 66.4, 38.3, 38.2, 27.2, 25.8, 7.0, 4.9; $^{31}$P NMR (162 MHz, CDCl$_3$) δ 25.06(1P); MALDI-HRMS [M+H]$^+$ calcd for $C_{27}H_{41}O_6$PSiK 559.2042, found 559.2035.

(R)-Dibenzyl-1-hydroxy-3-((S)-2,2-dimethyl-1,3-dioxolan-4-yl)-ethylphosphonate (5a). To a solution of 6a (400 mg, 0.77 mmol) in MeOH (8 mL) was added NH$_4$F (285 mg, 7.7 mmol). The resulting mixture was stirred at rt for 3 h, concentrated and chromatographed on silica gel (hexanes/EtOAc, 1:2) to afford pure product 5a (300 mg, 96%) as a colorless oil. $[α]^D_{20}$=−8.8 (c 1.2, CHCl$_3$); NMR(400 MHz, CDCl$_3$) δ 7.33 (m, 10H), 5.12-5.01 (m, 4H), 4.48 (br, OH, 1H), 4.36 (m, 1H), 4.22-4.17 (m, 1H), 4.06 (t, J=6.4 Hz, 1H), 3.56 (t, J=7.6 Hz, 1H), 2.00-1.90 (m, 2H), 1.36 (s, 3H), 1.32 (s, 3H); $^{13}$C NMR (101 MHz, CDCl$_3$) δ 136.5, 136.4, 128.8, 128.7, 128.2, 109.1, 73.2, 73.0, 69.8, 68.4, 68.36, 68.3, 66.4, 64.7, 35.5, 27.2, 25.9; $^{31}$P NMR (162 MHz, CDCl$_3$) δ 26.38 (1P); MALDI-HRMS [M +Na]$^+$ calcd for C$_{21}$H$_{27}$O$_6$PNa 429.1437, found 429.1428.

(S)-Dibenzyl-1-hydroxy-3-(((S)-2,2-dimethyl-1,3-dioxolan-4-yl)-ethylphosphonate (5b) was obtained from 6b in 94% yield analogously as described for compound 5a. [α]$^D_{20}$=−0.8 (c 1.0, CHCl$_3$); $^1$H NMR(400 MHz, CDCl$_3$) δ 7.35-7.32 (m, 10H), 5.14-5.03 (m, 4H), 4.30 (dt, J=12.8, 6.8 Hz, 1H), 4.15-4.10 (m, 1H), 4.03 (dd, J=8.0, 5.6 Hz, 1H), 3.96 (br, OH, 1H), 3.54 (dd, J=8.4, 7.2 Hz, 1H), 2.04-1.98 (m, 2H), 1.39 (s, 3H), 1.32 (s, 3H); $^{13}$C NMR (101 MHz, CDCl$_3$) δ 136.5, 136.4, 136.36, 128.8, 128.7, 128.3, 128.2, 109.7, 75.2, 75.1, 69.5, 68.6, 68.5, 68.4, 68.3, 68.1, 35.1, 27.1, 25.9; $^{31}$P NMR (162 MHz, CDCl$_3$) δ 25.36 (1P); MALDI-HRMS [M+Na]$^+$ calcd for C$_{21}$H$_{27}$O$_6$PNa 429.1437, found 429.1439.

(S)-Dibenzyl-[1S,3S-2,2-dimethyl-1,3-dioxolan-4-tert-butyldiphenylsilyl)-ethylphosphonate (7b) Phosphonate 5b (300 mg, 0.74 mmol) was dissolved in 10 mL MeOH, DOWEX-H$^+$(500 mg) was added to the mixture and stirred at overnight at rt. The mixture was filtered, the crude product was chromatographed on silica gel (MeOH/EtOAc, 1:10) to give the triol phosphonate (270 mg, 100%) as colorless oil. To a solution of the crude triol (140 mg, 0.38 mmol) and TBDP-SCl (0.15 mL, 0.57 mmol) in CH$_2$Cl$_2$ (5 mL), was added imidazole (40 mg, 0.59 mmol). After 3 h at rt., the solvents were removed, and the residue after the usual aqueous work-up was loaded onto a silica gel column. Purification (hexanes/EtOAc, 1:1) afforded diol (160 mg) as a colorless oil. The crude 1,3-diol (120 mg) was dissolved in 4 mL dimethoxypropane and 2 mL acetone, and treated with 15 mg TsOH. The mixture was stirred overnight and then purified on silica gel (hexanes/EtOAc, 2:1) to give 7b (110 mg) as colorless oil. [α]$^D_{20}$=−7.6 (c 1.2, CHCl$_3$); $^1$HNMR (400 MHz, CDCl$_3$) δ 7.58-7.55 (m, 4H), 7.32-7.22 (m, 16H), 5.09-4.98 (m, 4H), 4.21 (td, J=12.4, 2.4 Hz, 1H), 3.84 (m, 1H), 3.59 (dd, J=10.8, 4.8 Hz, 1H), 3.44 (dd, J=10.0, 5.6 Hz, 1H), 1.73-1.56 (m, 2H), 1.30 (s, 3H), 1.25 (s, 3H), 0.95 (s, 9H); $^{13}$C NMR (101 MHz, CDCl$_3$) δ 136.6, 136.56, 136.5, 135.9, 135.89, 133.8, 133.7, 129.93, 129.9, 128.8, 128.78, 128.63, 128.6, 128.1, 128.0, 127.9, 127.88, 99.6, 99.5, 69.5, 69.3, 68.5, 68.4, 68.38, 68.3, 67.4, 65.6, 29.8, 27.96, 27.9, 27.1, 19.5, 19.2; $^{31}$P NMR (162 MHz, CDCl$_3$) δ 22.62 (IP); MALDI-HRMS [M+Na]$^+$ calcd for C$_{37}$H$_{45}$BrO$_6$PSiNa 667.2615, found 667.2638.

(R)-Dibenzyl-[1S,3S-2,2-dimethyl-1,3-dioxolan-4-tert-butyldiphenylsilyl)-ethylphosphonate (7a) was obtained from 5a analogously as described for compound 7b. [α]$^D_{20}$=−29.6 (c 1.0, CHCl$_3$); $^1$H NMR (400 MHz, CDCl$_3$) δ 7.69 (dd, J=7.6, 1.2 Hz, 2H), 7.55 (dd, J=7.6, 1.2 Hz, 2H), 7.37-7.02 (m, 16H), 4.83-4.66 (m, 4H), 4.15-4.09 (m, 2H), 3.74 (dd, J=8.0, 6.0 Hz, 1H), 3.11 (t, J=8.0 Hz, 1H), 1.95-1.74 (m, 2H), 1.15 (s, 3H), 1.05 (s, 3H), 0.95 (s, 9H); $^{13}$C NMR (101 MHz, CDCl$_3$) δ 136.5, 136.4, 132.9, 132.8, 130.1, 129.9, 128.7, 128.69, 128.54, 128.5, 128.3, 128.2, 127.72, 127.7, 109.0, 71.7, 71.6, 69.4, 68.3, 67.8, 67.7, 67.5, 67.4, 66.6, 36.7, 27.2, 25.8, 19.9; $^{31}$P NMR (162 MHz, CDCl$_3$) δ 25.74 (1P); MALDI-HRMS [M+Na]$^+$ calcd for C$_{37}$H$_{45}$BrO$_6$PSiNa 667.2615, found 667.2617.

(R)-Dibenzyl-1-hydroxy-2-((S)-2,2-dimethyl-1,3-dioxolan-4-yl)-ethylphosphonate (8a). CBr$_4$ (1.3 g) in 5 mL toluene was added to a solution of 5a (1.0 g, 2.46 mmol) and PPh$_3$ (1.0 g) in 80 mL mixture solvents of toluene:pyridine (12:1). The mixture was stirred at rt under Ar for 30 min, and then was warmed to 80° C. for 8H. The organic phase was concentrated, and the residue was chromatographed on silica gel (hexanes/EtOAc, 10:7) to afford pure syn bromophosphonate 8a (120 mg, 11%) as a yellow oil. [α]$^D_{20}$=+11.0 (c 0.3, CHCl$_3$); $^1$H NMR(400 MHz, CDCl$_3$) δ 7.29-7.27 (m, 10H), 5.10-4.96 (m, 4H), 4.26 (dt, J=13.2, 6.8 Hz, 1H), 3.91 (dd, J=8.4, 6.0 Hz, 1H), 3.77-3.71 (m, 1H), 3.40-3.36 (dd, J=8.8, 6.4 Hz, 1H), 2.26-2.16 (m, 2H), 1.31 (s, 3H), 1.22 (s, 3H); $^{13}$C NMR (101 MHz, CDCl$_3$) δ 136.1, 136.0, 135.97, 135.9, 128.9, 128.87, 128.4, 128.3, 109.5, 74.1, 74.0, 69.6, 69.57, 69.2, 69.1, 68.8, 37.8, 37.7, 36.2, 27.2, 25.7; $^{31}$P NMR (162 MHz, CDCl$_3$) δ 21.50 (1P); MALDI-HRMS [M+Na]$^+$ calcd for C$_{21}$H$_{26}$BrO$_5$PNa 491.0593, found 491.0588.

(S)-Dibenzyl-1-bromo-3-((S)-2,2-dimethyl-1,3-dioxolan-4-yl)-ethylphosphonate (8b) was obtained from 5b in 45% yield analogously as described for compound 8a. [α]$_{20}$=−24.3 (c 1.1, CHCl$_3$); $^1$H NMR(400 MHz, CDCl$_3$) δ 7.35-7.32 (m, 10H), 5.16-5.03 (m, 4H), 4.37-4.31 (m, 1H), 4.16-4.09 (m, 1H), 4.06 (dd, J=8.4, 6.4 Hz, 1H), 3.56 (dd, J=8.0, 5.6 Hz, 1H), 2.30-2.21 (m, 1H),1.99-1.90 (m, 1H), 1.33 (s, 3H), 1.32 (s, 3H); $^{13}$C NMR (101 MHz, CDCl$_3$) δ 136.2, 136.1, 136.07, 136.0, 128.9, 128.83, 128.3, 109.6, 73.0, 72.9, 69.5, 69.4, 69.1, 69.04, 69.0, 39.7, 38.1, 37.2, 27.4, 25.8; $^{31}$P NMR (162 MHz, CDCl$_3$) δ 22.02 (1P); MALDI-HRMS [M+Na]$^+$ calcd for C$_{21}$H$_{26}$BrO$_5$PNa 491.0593, found 491.0582.

Dibenzyl-[(1R)-bromo-(3S)-4-bishydroxybutyl]phosphonate (9a). Phosphonate 8a (250 mg, 0.53 mmol) was dissolved in 8 mL MeOH and stirred with DOWEX-H$^+$ (300 mg) overnight at rt. The mixture was filtered, and the crude product was chromatographed on silica gel (MeOH/EtOAc, 1:10) to give the syn phosphonate 9a (210 mg, 93%) as colorless oil. [α]$^D_{20}$=−14.9 (c 1.3, CHCl$_3$); $^1$H NMR(400 MHz, CDCl$_3$) δ 7.34-7.32 (m, 10H), 5.15-5.03 (m, 4H), 4.09-4.03 (m, 1H), 3.59 (br, OH, 2H), 3.57 (dd, J=11.6, 3.6 Hz, 1H), 3.45 (dd, J=11.2, 6.4 Hz, 1H), 2.25-2.17 (m); $^{13}$C NMR (101 MHz, CDCl$_3$) δ 135.9, 135.88, 135.77, 135.7, 128.97, 128.95, 128.9, 128.4, 128.3, 70.0, 69.9, 69.8, 69.7, 69.3, 69.26, 65.9, 38.5, 37.1, 36.9; $^{31}$P NMR (162 MHz, CDCl$_3$) δ 22.86 (1P); MALDI-HRMS [M+Na]$^+$ calcd for C$_{18}$H$_{22}$BrO$_5$PNa 451.0280, found 451.0266.

Dibenzyl-[(1S)-Bromo-(3S)-4-bishydroxybutyl]phosphonate (9b) was obtained from 8b in 95% yield analogously as described for compound 9a. [α]$^D_{20}$=−20.2 (c 0.8, CHCl$_3$); $^1$H NMR(400 MHz, CDCl$_3$) δ 7.23-7.22 (m, 10H), 5.01-4.94 (in, 4H), 4.23-4.17 (m, 1H), 3.87-3.84 (m, 2H), 3.58 (m, 2H), 3.53 9dd, J=13.2, 3.2 Hz, 1H), 3.34 (dd, J=13.2, 6.4 Hz, 1H), 2.13-2.04 (m, 1H), 1.80-11.71 (m, 1H); $^{13}$C NMR (101 MHz, CDCl$_3$) δ 136.0, 135.9, 135.88, 135.8, 128.9, 128.3, 70.0, 69.6, 69.5, 69.3, 69.28, 69.2, 69.0, 66.7, 39.6, 37.9, 35.8; $^{31}$P NMR (162 MHz, CDCl$_3$) δ 22.99 (IP); MALDI-HRMS [M+Na]$^+$ calcd for C$_{18}$H$_{22}$BrO$_5$PNa 451.0280, found 451.0270.

Dibenzyl-[(1S)-Bromo-(3S)-hydroxy-4-(palmitoyloxy) butyl]phosphonate (10b). To a solution of the diol 9b (210 mg, 0.49 mmol) and palmitic acid (140 mg, 0.55 mmol) in CH$_2$Cl$_2$ (10 mL), was added EDCl (210 mg, 1.09 mmol) and catalytic amount of DMAP. After stirring for 12 h at rt, the solvents were removed; after the usual aqueous work-up, the residue was loaded on a silica gel column and purification (hexanes/EtOAc, 10:7) afforded 10b (230 mg, 71%) as a colorless oil. [α]$^D_{20}$=−12.5 (c 1.2, CHCl$_3$); $^1$H NMR(400 MHz, CDCl$_3$) δ 7.35-7.33 (m, 10H), 5.15-5.03 (m, 4H), 4.28-4.22 (m, 1H), 4.12-3.98 (m, 3H), 2.92 (br, OH, 1H), 2.31 (t, J=7.2 Hz, 2H), 2.18-2.09 (m, 1H), 1.97-1.88 (m, 1H), 1.63-1.56 (m, 2H), 1.25 (m, 24H), 0.88 (t, J=6.8 Hz, 31-1); $^{13}$C NMR (101 MHz, CDCl$_3$) δ 174.16, 136.1, 136.03, 136.0, 135.9, 128.9, 128.3, 69.5, 69.4, 69.2, 69.1, 68.1, 67.0, 66.9, 39.4, 37.8, 36.2, 34.3, 32.2, 29.9, 29.89, 29.8, 29.7, 29.6, 29.5, 29.4, 25.1, 22.9, 14.4; $^{31}$P NMR (162 MHz, CDCl$_3$) δ 22.55 (1P); MALDI-HRMS [M+Na]$^+$ calcd for C$_{34}$H$_{52}$BrO$_6$PNa 689.2577, found 689.2573.

Dibenzyl-[(1R)-Bromo-(3S)-hydroxy-4-(palmitoyloxy)butyl]phosphonate (10a). The selective carbodiimide-mediated palmitoylation of the syn diol 9a was unsuccessful and a different method was used. Thus, to a solution of the diol 9a (83 mg, 0.19 mmol) in CH$_2$Cl$_2$ (2 mL) at −78° C., was added palmitoyl chloride (60 mg, 0.19 mmol) and 2,4,6-collidine (50 uL, 0.40 mmol). After 4 h at −78° C., the reaction was diluted with CH$_2$Cl$_2$, the mixture was washed twice with 1 N HCl, dried over Na$_2$SO$_4$, and concentrated. The residue was loaded onto a silica gel column and purified (hexanes/EtOAc, 10:7) to give 10a (82 mg, 63%) as a colorless oil. $[\alpha]^D{}_{20}=-6.0$ (c 0.3, CHCl$_3$); $^1$H NMR(400 MHz, CDCl$_3$) δ 7.28-7.27 (m, 10H), 5.10-4.94-(m, 4H), 4.17-4.11 (dt, J=10.4, 6.0 Hz, 1H), 4.02-3.93 (m,3H), 2.23 (t, J=7.6 Hz, 2H), 2.18 (t, J=6.0 Hz, 1H), 2.13 (t, J=6.0 Hz, 1H), 1.53 (m, 2H), 1.18 (m, 24H), 0.81 (t, J=6.8 Hz, 3H); $^{13}$C NMR (101 MHz, CDCl$_3$) δ 174.1, 136.1, 135.9, 135.8, 135.7, 128.99, 128.96, 129.91, 128.9, 128.4, 128.3, 70.0, 69.9, 69.3, 69.2, 67.5, 67.4, 67.3, 38.3, 37.7, 36.69, 34.3, 32.2, 29.92, 29.9, 29.8, 29.7, 29.6, 29.5, 29.4, 25.1, 22.9, 14.4; $^{31}$P NMR (162 MHz, CDCl$_3$) δ 22.78 (1P); MALDI-HRMS [M+Na]$^+$ calcd for C$_{34}$H$_{52}$BrO$_6$PNa 689.2577, found 689.2626.

1(S)-Bromo-3(S)-hydroxy-4-(palmitoyloxy)butyl]phosphonate (1b). To a solution of phosphonate 10b (120 mg, 0.18 mmol) in 8 mL EtOAc was added PtO$_2$ (6 mg). The mixture was stirred under 1 atm H$_2$ atmosphere for 20 min, filtered and concentrated to give anti isomer 1b (87 mg, 100%). $[\alpha]^D{}_{20}=-32.1$ (c 0.5, CDCl$_3$); $^1$H NMR(400 MHz, CDCl$_3$) δ 4.11-4.00 (m, 4H), 2.28 (t, J=7.6 Hz, 2H), 2.15-2.08 (m, 1H), 1.94-1.85 (m, 1H), 1.63-1.56 (m, 2H), 1.18 (m, 24H), 0.80 (t, J=7.2 Hz, 3H); $^{13}$C NMR (101 MHz, CDCl$_3$) δ 174.6, 68.1, 66.8, 66.7, 40.9, 39.3, 36.6, 34.2, 32.1, 29.8, 29.78, 29.7, 29.6, 29.5, 29.4, 29.3, 25.0, 22.8, 14.1; $^{31}$ P NMR (162 MHz, CDCl$_3$) δ 20.21 (1P); MALDI-HRMS [M+Na]$^+$ calcd for C$_{20}$H$_{40}$BrO$_6$PNa 509.1638, 511.1621, found 509.1634, 511.1557.

1(R)-Bromo-3(S)-hydroxy-4-(palmitoyloxy)butyl]phosphonate (1a) was obtained from 10a in 94% yield analogously as described for compound 1b. $[\alpha]^D{}_{20}=+3.2$ (c 0.5, CHCl$_3$); $^1$H NMR(400 MHz, CDCl$_3$) δ 4.13 (m, 1H), 4.05-4.00 (m, 2H), 3.95-3.98 (m, 1H), 2.28 (t, J=7.6 Hz, 2H), 2.25-2.08 (m, 2H), 1.54 (m, 2H), 1.18 (m, 24H), 0.80 (t, J=6.8 Hz, 3H); $^{13}$C NMR (101 MHz, CDCl$_3$) δ 174.6, 67.6, 67.5, 67.1, 39.5, 37.9, 37.4, 34.2, 32.1, 29.8, 29.78, 29.7, 29.6, 29.5, 29.4, 29.3, 24.98, 22.8, 14.1; $^{31}$P NMR (162 MHz, CDCl$_3$) δ 19.64 (1P); MALDI-HRMS [M+Na]$^+$ calcd for C$_{20}$H$_{40}$BrO$_6$PNa 509.1638, 511.1621, found 509.1639, 511.1605.

III. Pharmacological Studies

Receptor activation using Ca$^{2+}$ mobilization assay for diastereomers of 1 (also represented as 19b). The rat hepatoma (RH7777) cell lines individually expressing either LPA$_1$, LPA$_2$, LPA$_3$ or LPA$_5$ receptors and Chinese hamster ovary (CHO) cell line were analyzed to examine agonism and antagonism. Wild type RH7777 cells do not respond to LPA with changes in [Ca$^{2+}$]$_i$. CHO cells stably expressing either vector or LPA$_4$ were kindly gifted from Dr. Shimizu (University of Tokyo, Tokyo, Japan).

Stable transformants of LPA$_{1/2/3}$ receptors. RH7777 cells stably expressing each receptor were plated onto poly-L-lysine (PLL) (0.1 mg/mL)-coated black-wall clear-bottom 96-well plates (Corning Incorporated Life Sciences, Acton, Mass.) at a density of 5×10$^4$ cells/well and cultured overnight. The following day, the culture medium was replaced with modified Krebs buffer (120 mM NaCl, 5 mM KCl, 0.62 mM MgSO4, 1.8 mM CaCl2, 10 mM HEPES, 6 mM glucose, pH 7.4), and the cells were serum starved for 6 h. Subsequently, cells were loaded with Fura-2 AM (Invitrogen, Carlsbad, Calif.) for 35 min in modified Krebs buffer containing 2% (v/v) pluronic acid.

Stable transformants of LPA$_4$. CHO cells stably expressing either vector or LPA4 were plated on non-coated 96 well plates at a density of 4×10$^4$ cells/well and cultured overnight. The following day, cells were loaded with Fura-2 AM for 1 h in modified Krebs buffer containing 2% (v/v) pluronic acid and 2.5 mM probenecid.

Transient transfection of LPA$_5$. RH7777 cells in a 10-cm dish at a density of 2×10$^6$/dish were transfected with 2 μg of plasmid DNA with Effectene (Qiagen, Valencia, Calif.) according to the manufacturer's instructions for 24 h, then replated onto PLL-coated 96-well plates at a density of 5×10$^4$ cells/well and cultured overnight. The following day, the culture medium was then replaced with modified Krebs buffer, and the cells were serum starved for 4 h. Subsequently, cells were loaded with Fura-2 AM for 30 min in modified Krebs buffer containing 2% (v/v) pluronic acid.

After incubating the cells with Fura-2 AM, the cells were rinsed with Krebs buffer and changes in the intracellular Ca$^{2+}$ concentration were monitored by determining the ratio of emitted light intensities at 520 nm in response to excitation at 340 and 380 nm using FLEXstation II (Molecular Devices, Sunnyvale, Calif.). Each well was monitored for 80-120 sec. For testing agonist activity of the compounds, the test compounds were added automatically after 15 sec of baseline measurement. To determine antagonist properties, varying concentrations of the compounds were mixed with a constant concentration of LPA and responses were monitored. Each test was performed in quadruplicate. EC$_{50}$, IC$_{50}$, and K$_i$ values were calculated by fitting a sigmoid function to data points with the nonlinear curve-fitting feature of Kaleida-Graph (Synergy Software, Essex Junction, Vt.).

Receptor activation using Ca$^{2+}$ mobilization assay. The assay for mobilization of intracellular Ca$^{2+}$ was performed as described. Briefly, rat hepatoma RH7777 cells stably expressing human LPA$_1$, LPA$_2$, or LPA$_3$, and CHO cells stably expressing LPA$_4$, were loaded with Fura-2 AM (Molecular Probes). Using a FLEXStation (Molecular Devices, Sunnyvale, Calif.), changes in intracellular Ca$^{2+}$ concentration were monitored. Ligand-induced changes in fluorescence were monitored for 80-120 seconds. Ca$^{2+}$ transients were quantified automatically by calculating the difference between maximum and baseline ratio values for each sample. To determine antagonist properties, different concentrations of each analogue were mixed with either palmitoyl (16:0) or oleoyl (18:1) LPA (200 nM for LPA$_1$ and LPA$_3$, 10 nM for LPA$_2$, and 400 nM for LPA$_4$) (Avanti Polar Lipids, Inc., Shearwater, Ala.) and responses were recorded. Each test was performed in quadruplicate. EC$_{50}$, IC$_{50}$, and K$_i$ values were calculated as described. The ligand properties of the compounds were evaluated using Ca$^{2+}$ mobilization assay for assessing the activation/inhibition of LPA$_1$, LPA$_2$, and LPA$_3$ expressed in RH7777 cells and LPA$_4$ expressed in CHO cells. Table 1 illustrates calcium responses elicited through the activation of human LPA$_1$, LPA$_2$, LPA$_3$ and LPA$_4$ receptors. These cell lines have been used extensively for the characterization of LPA GPCR ligands because RH7777 cells are intrinsically unresponsive to LPA and CHO cells show minimal endogenous responses to LPA unless transfected with LPA$_4$.

The α-halomethylene phosphonate analogues showed partial agonist-antagonist duality based on the acyl chain employed. Thus, α-chloromethylene phosphonate 18a with an oleoyl chain showed a mixed agonist-antagonist profile, with agonist effects on LPA$_1$, LPA$_3$, and LPA$_4$, showing quite high selectivity for activation of LPA$_1$ as a partial agonist with an EC$_{50}$ of 528 nM. Surprisingly, 18a showed an IC$_{50}$ of 1.7 µM as an antagonist of the LPA$_2$ receptor. In contrast to the mixed activities of the oleoyl α-chloromethylene phosphonate, the palmitoyl analogue 18b was a pan-antagonist with highest potency towards LPA$_2$ (IC$_{50}$=855 nM) and LPA$_3$ (IC$_{50}$=175 nM). An analogous mixed profile of agonist and antagonist effects was observed for the oleoyl α-bromomethylene analogue 19a, with partial LPA$_3$ agonist activity, but had strong antagonist activities towards LPA$_1$, LPA$_2$, and LPA$_4$ receptors. As observed for 18b, the palmitoyl α-bromomethylene phosphonate 19b was an LPA GPCR pan-antagonist with highest potency towards the non-EDG LPA receptor LPA$_4$.

To date, there have been no reports of selective agonists or antagonists for LPA$_4$ (p2y9/GPR23), thereby limiting the search for the physiological role of this new receptor. In this series of substituted methylene phosphonate analogues, the methylene phosphonate analogues 20a and 20b (FIG. 4) as well as the oleoyl a-hydroxymethylene phosphonate analogue 22a (FIG. 4) were weak LPA$_4$ agonists (Table 1). In general, analogues with oleoyl chains were more potent than those with palmitoyl chains, consistent with the preference LPA$_4$ for unsaturated acyl chains. The most significant activity observed, however, was the discovery that both α-bromomethylene phosphonate analogs 19a and 19b were LPA$_4$ antagonists, with the palmitoyl analogue 19b showing an IC$_{50}$ value of 266 nM for LPA$_4$. Analogue 19b is therefore the first reported antagonist of the LPA$_4$ receptor, and may be a useful pharmacological tool.

In the next stage of this investigation, the pharmacological properties of the mixed diastereomers 1 as well as the separately synthesized diastereomers 1a and 1b were evaluated using a Ca$^{2+}$ mobilization assay for assessing the activation/inhibition of LPA$_1$, LPA$_2$, LPA$_3$, and LPA$_5$ expressed in RH7777 cells and LPA$_4$ expressed in CHO cells as described above.

Table 2 illustrates calcium responses elicited through the activation of human LPA$_1$, LPA$_2$, LPA$_3$, LPA$_4$, and LPA$_5$ receptors to syn-BrP-LPA 1a, anti-BrP-LPA 1b and BrP-LPA 1. These cell lines have been used extensively for the characterization of LPA GPCR ligands because RH7777 cells are intrinsically unresponsive to LPA and CHO cells show minimal endogenous responses to LPA unless transfected with LPA$_4$.

The diastereomeric mixture BrP-LPA 1 showed pan-antagonist activity for stably transfected receptors LPA$_{1-4}$ and potent inhibition of ATX activity, with submicromolar potency towards LPA$_2$, modest inhibition of LPA activation of LPA$_4$, and weak partial agonism for the transiently transfected LPA$_5$. The syn-BrLPA 1a was a pan-antagonist with showing K$_i$ values of 273 nM, 250 nM and 1830 nM for LPA$_1$, LPA$_2$ and LPA$_3$, respectively. By comparison, anti-BrP-LPA 1b was less potent at LPA$_1$ and more potent at LPA$_3$, with K$_i$ values of 752 nM, 241 nM and 623 nM for LPA$_1$, LPA$_2$ and LPA$_3$, respectively. Neither diastereomer showed full antagonism of LPA$_4$, and only anti-BrP-LPA 1b showed inhibition of LPA$_5$ (K$_i$=376 nM).

PPARγ activation assay. PPARγ activation was performed using CV-1 cells transfected with an acyl-coenzyme A oxidase-luciferase (PPRE-Acox-Rluc) reporter gene construct as previously reported. Briefly, CV-1 cells were plated in 96-well plates at a density of 1×10$^4$ cells per well in Dulbecco's modified Eagle's medium supplemented with 10% fetal bovine serum. The next day, the cells were transiently transfected with 125 ng of pGL3-PPRE-Acox-Rluc, 62.5 ng of pcDNA3.1 PPARγ, and 12.5 ng of pSV-β-galactosidase (Promega) using LipofectAMINE 2000 (Invitrogen). Twenty-four hours after transfection, cells were treated with OptiMEM (Invitrogen) containing 10 µM Rosiglitazone or 10 µM of the test analogue dissolved in DMSO for 20 h. Luciferase and β-galactosidase activities were measured with Steady-Glo® Luciferase Assay System (Promega) and the Galacto-Light Plus™ system (Applied Biosystems), respectively. Samples were run in quadruplicate and the mean ±standard errors were calculated. Data are representative of at least two independent transfections.

In addition to LPA GPCRs receptors, LPA activates the nuclear transcription factor PPARγ. Many agents have been reported to be agonists of PPARγ, including the thiazolidinedione family represented by Rosiglitazone (Rosi), oxidized phospholipids, fatty acids, eicosanoids, and oxidized LDL. LPA and the alkyl ether analog of LPA directly bind to the ligand-binding domain of PPARγ. The activation of PPARγ is direct, and is enhanced when the LPA entry into cells was facilitated by carrier amine sulfonamides capable of increasing the transmembrane movement of LPA. Each of the unsubstituted and α-substituted methylene phosphonate LPA analogues 20, 22, 18 and 19, both oleoyl and palmitoyl analogues, were tested for PPARγ activation in CV-1 cells expressing an acyl-coenzyme A oxidase-luciferase (PPRE-Acox-Rluc) reporter gene construct. As shown in Table 1, none of these compounds activated PPRE-Acox-Rluc reporter.

Autotaxin Assay. This assay utilizes FS-3 (Echelon Biosciences, Inc. Salt Lake City, Utah) as substrate and recombinant ATX-HA. For analysis, 50 µl of ATX-HA (0.25 µg) in assay buffer (Tris 50 mM, NaCl 140 mM, KCl 5mM, CaCl$_2$ 1 mM, MgCl$_2$ 1 mM, pH 8.0) was mixed with 25 µl of FS-3 (1 µM final concentration in assay buffer) and 25 µl of test compound dissolved in assay buffer containing 1:1.5 bovine serum albumin in 96-well plate. FS-3 fluorescence was monitored using FLEXstation fluorescence plate reader at a time zero and after 2 hours of incubation at 37° C. at excitation and emission wavelengths of 485 nm and 538 nm, respectively. Data was normalized to the corresponding vehicle control and the mean±standard deviation of triplicate wells were expressed as percent ATX inhibition. IC$_{50}$, and K$_i$ values were calculated as described.

The inhibition of ATX by the α-substituted methylene phosphonate analogues 20, 22, 18, and 19 was tested at a single dosage (10 µM) and compared to the ATX inhibitory effects of LPA (18:1) and LPA (16:0) at the same concentration (Table 3). ATX activity was measured by the hydrolysis of the fluorogenic lysoPC analogue FS-3, which has a K$_m$ value of 6.3 µM. The results showed that all of the analogues, the unsubstituted as well as each of the α-substituted phosphonates, inhibited ATX at a concentration of 10 µM. Although dose-response data remain to be determined, in this preliminary screen, three compounds (20a, 19a, and 19b) were revealed as potent inhibitors of >90% enzyme activity. The oleoyl unsubstituted phosphonate analogue 20a inhibited 99.8% of ATX activity. In contrast, the oleoyl α-OH analogue 22a showed 74.7% inhibition. The mixed epimers of the palmitoyl α-OH analogue 22b showed 54.1% inhibition; when the pure synthetic diastereomers were tested, the (S,S) isomer 24a showed 56.6% inhibition and the (S,R) isomer 24b showed 43.4% inhibition, respectively. Only a marginal discrimination of diastereomers was found. Finally, both the oleoyl and palmitoyl α-Br analogues 19a and 19b inhibited >90% of ATX activity. As both a pan-LPA GPCR antagonist and a potent inhibitor of ATX, this single molecule can pack a "one-two" punch in both significantly lowering LPA production and by blocking activation of all cell-surface LPA receptors.

Figure 5:
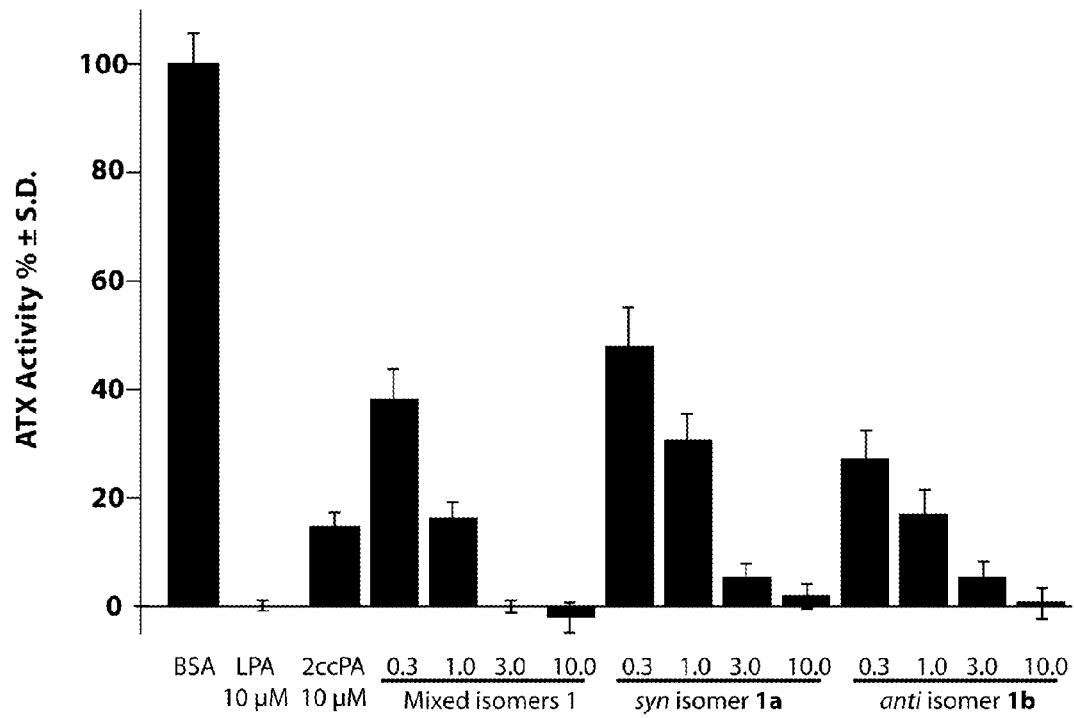
FIG. 5 shows inhibition of lysophospholipase D activity of ATX. Assays were conducted using fluorogenic substrate FS-3, an analogue of lysophosphatidylcholine. LPA 18:1 and 2-carba cyclic phosphatidic acid 16:1 (2ccPA), known inhibitors of ATX, were positive controls.
Figure 6:
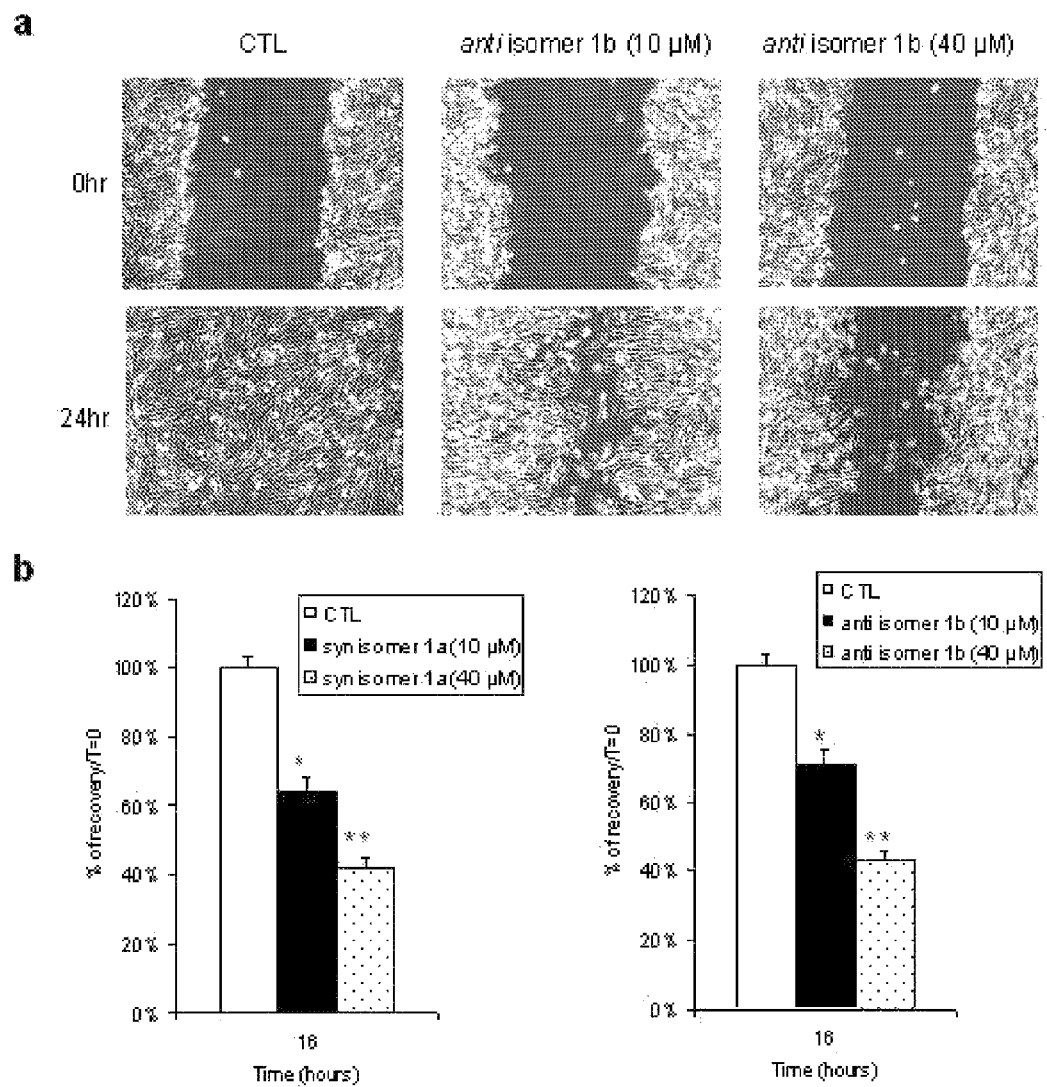
FIG. 6 shows the effect of syn-1a and anti-1b BrP-LPA diastereomers on MDA-MB-231 cell migration. Confluent MDA-MB-231 cells were scratched with a pipette tip and then treated with pure syn-1a or anti-1b (10 and 40 µM) and compared with untreated cells (CTL) at 24 h (panel a). Cell migration at 0 and 24 h post-injury was assessed photographically, and then measured and quantified using Image J. Quantification for the anti-BrP-LPA 1b and syn-BrP-LPA 1a are shown in panel b. Asterisks indicate significant differences from control (CTL) at $p<0.001$ (*) and $p<0.0001$ (**).

The inhibition of ATX by BrP-LPA 1, syn-BrP-LPA 1a, and anti-BrP-LPA 31b, was measured at concentrations of 0.3 to 10 µM and compared to the ATX inhibitory effects of 10 µM LPA (18:1) and 10 µM 2ccLPA (16:1) (FIG. 5). ATX activity was measured by the hydrolysis of the fluorogenic lysoPC analogue FS-3, which has a $K_m$, value of 6.3 µM. The results showed that each of the analogues 1 inhibited greater than 98% of ATX at a concentration of 10 µM. A clear dose-response effect on inhibition was observed for both syn-BrP-LPA 31a and anti-BrP-LPA 1b, with the apparent $IC_{50}$ value for 1b showing that the anti isomer was considerably more potent than the syn isomer ($IC_{50}$=ca. 300 nM).

Inhibition of migration. MDA-MB-231 cells were plated in triplicate into six-well plates at a concentration of $3 \times 10^5$ cells per well. Approximately 48 hours later, the confluent cells were carefully scratched using sterile pipette tips. Nonadherent cells and cellular debris were removed by washing with PBS. Fresh medium with or without various concentrations of BrP-LPA 1, syn-BrP-LPA 1a, or anti-BrP-LPA 1b (1-100 µM) were added to the wounded monolayers. Cells were observed under the microscope and digitally photographed at different times. Inhibition of migration was assessed when the wound in the control was closed and quantified by using ImageJ.

As both a pan-LPA GPCR antagonist and a potent inhibitor of ATX, this single molecule acts as a dual inhibitor, both significantly lowering LPA production and by blocking activation of all cell-surface LPA receptors. Such a molecule has clear therapeutic potential to inhibit the role of LPA in promoting cell migration, invasion, and proliferation. Thus, the effect of the LPA antagonists on the cell migration of metastatic potential MDA-MB-231 breast cancer cells by using a scratch wound healing assay was evaluated (FIG. 6a, asterisks indicate significant differences from control (CTL) at p<0.001 (*) and p<0.0001 (**)). The relative expression of LPA GPCRs in MDA-MB-231 cells is $LPA_1 > LPA_2 \gg LPA_3$. $LPA_1$ is the most important GPCR mediating cell migration of normal and neoplastic cells. After treatment with different concentrations of the pure diastereomers 1a and 1b, and the mixture BrP-LPA 1, cells were allowed to migrate into the denuded area for 0, 16 and 24 h. By 24 h, untreated control cells completely filled the scratched area. Treatment with syn-BrP-LPA 1a and anti-BrP-LPA 1b at 10 and 40 µM inhibited the MDA-MB-231 cell migration (FIG. 6b). FIG. 12b shows that the migration of MB-231 cells was significantly decreased by 57% (p<0.05) by 40 µM anti-BrP-LPA 1b when compared to control. The mixed diastereomers showed intermediate inhibition of cell migration (data not shown). The inhibition of cell migration at all time points indicates that these effects are not due to its ability to inhibit cell proliferation.

Inhibition of invasion. The invasive behavior of cells was determined in vitro by using 24-well transwell inserts with an 8 µm pore size PET membrane which were coated with Matrigel basement membrane matrix. A suspension of cells (100 µL of $5 \times 10^4$) in serum-free medium with or without 10 µM syn-BrP-LPA 1a or anti-BrP-LPA 1b was added to triplicate inserts, and 600 µL medium supplemented with serum was used as a chemoattractant in the lower chamber. After 24 h of incubation, the cells that did not invade through the pores were removed, and cells that passed through the filter on the underside of the membrane were stained with the Diff-Quick Staining Set and counted. Ten fields of cells were counted for each well, and the mean number of cells per field was calculated. Each experiment was performed in triplicate and repeated at least twice.

Figure 7:
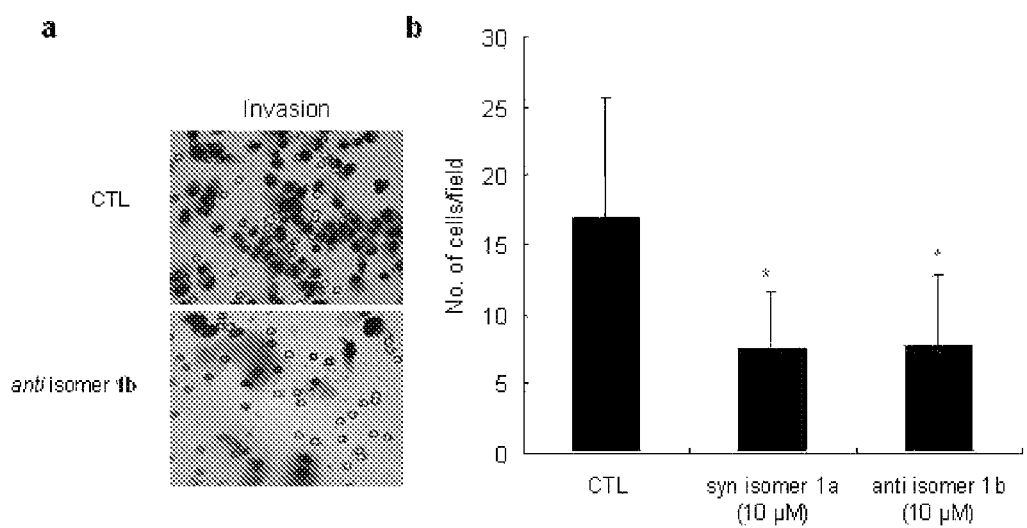
FIG. 7 shows the effects on invasion of MDA-MB-231 cells through Matrigel-coated membranes. Panel a: representative fields of cells that invaded under the membrane through the Matrigel. Panel b: Ten fields of each treatment and control group were counted, and the mean value of invading cells were calculated. Asterisks indicate significant difference from control at p<0.05 for syn isomer 1a and p<0.01 for anti isomer 1b.
Figure 8:
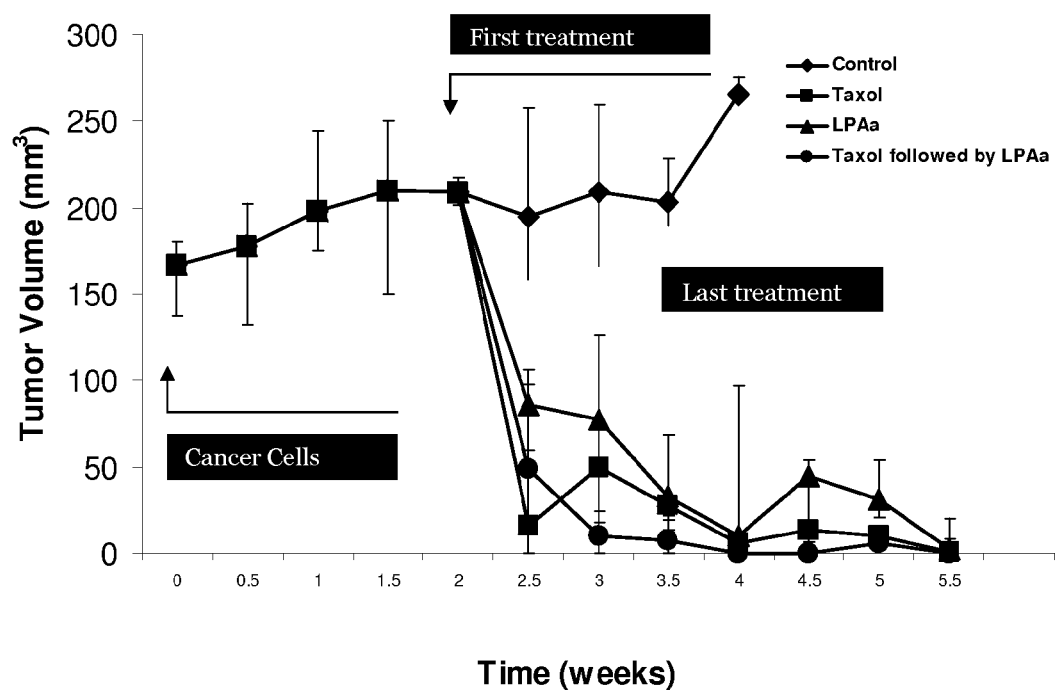
FIG. 8 shows reduction of tumor volume over time using the mixed diastereoisomers of the α-bromo LPA analog 1 (an LPA receptor antagonist, or "LPAa" in the figure) to treat nude mice with xenografted, engineered tumors generated by mammary fat pad injection of MDA-MB-231 cells in a synthetic extracellular matrix.

FIG. 7 shows the effects on invasion of MDA-MB-231 cells through Matrigel-coated membranes. Panel a: representative fields of cells that invaded under the membrane through the Matrigel. Panel b: Ten fields of each treatment and control group were counted, and the mean value of invading cells were calculated. Asterisks indicate significant difference from control at p <0.05 for syn isomer 1a and p<0.01 for anti isomer 1b. In an in vitro invasion assay using a modified Boyden chamber, MDA-MB-231 cells showed prominent invasion through Matrigel-coated transwell membranes. Treatment with either anti-BrP-LPA 1a or syn-BrP-LPA 1b inhibited the invasion by approximately 52% (p<0.05), but the potency of the two isomers was not significantly different in this assay. These results suggest that diastereomers of LPA analogue 1a and 1b are sufficient to inhibit the migration and invasion in vitro.

Preparation of the cross-linkable sECM hydrogel. The injectable sECM (Extracel™) was obtained from Glycosan BioSystems. Solutions of 2.5% (w/v) CMHA-S and 3%(w/v) gelatin-DTPH were prepared by dissolving CMHA-S and gelatin-DTPH in ddH$_2$O. A solution of 4% PEGDA was prepared by dissolving PEGDA in Dulbecco's phosphate-buffered saline (DPBS). These materials were prepared using techniques disclosed in International Publication No. WO 2005/056608, which is incorporated by reference in its entirety.

Cell Culture. MDA-MB-231 cell line was used in this study, and passaged 5 times from the cell line obtained from American Type Culture Collection (ATCC). Cells were cultured with DMEM medium supplemented with 10% fetal bovine serum (FBS), 100 U/mL penicillin, 100 ug/mL Streptomycin in T175 flasks.

Orthotopic Human Breast Cancer Models. 4-week-old female athymic nude mice (Charles River Laboratories) were anesthetized by intraperitoneal injection of ketamine (80 mg/kg) and xylazine (10 mg/kg),according to the protocol approved by the University of Utah Institutional Animal Care and Use Committee (IACUC). Then the thoracic skin was sterilized with iodine and alcohol swabs.

MDA-MB-231 were trypsinized and resuspended in 2.5% CMHA-S and 3% gelatin-DTPH (v:v=1:1). Then, one volume of 4% PEGDA solution was added to four volumes of the cell suspension, and the resulting suspension was mixed gently by vortexing. The final cell concentration was $5 \times 10^7$ cells/ml. When the cell suspension was becoming viscous (ca. 3-5 min at 20° C.), 200 uL of gel was injected subcutaneously into the fourth mammary fat pad of each mouse, using a total of six mice per group.

The assessment of chemotherapy on breast cancer. The mice were randomly divided into 4 groups, including control (physiological saline), paclitaxel, LPA antagonist (19b), and paclitaxel followed by 19b. Six mice for each cell line were necessary to get statistically significant results according to literature. The control group received physiological saline i.p. injection twice per week starting at two weeks after the cell transplantation and ending at two weeks after the treatment. The treatment groups received i.p. administration of paclitaxel (10 mg/kg/day) or 19b (10 mg/kg/day) twice per week with the same period of control group. One additional group included 2 dose of paclitaxel followed by 2 dose of 19b with the same period of control group. The treatment was received subcutaneously twice per week for 2 weeks total.

The body weight and tumor size were measured twice per week, and general clinical status of the animals was also assessed every day. Perpendicular tumor diameters were measured using a vernier scale caliper and tumor volume estimated using the formula for ellipsoid: tumor weight $(mm^3)=[width(mm)^2 \times length(mm)]/2$. Data are expressed as median tumor areas with interquartile ranges.

Animals were euthanized at 4 weeks postinjection or once any signs of broken skin caused by the extension of tumor are found. Tumors were excised with surrounding tissues for histological evaluation. Analysis of variance was used to analyze the statistical difference on tumor growth between different groups. The results are in FIG. 8, where it is shown that the volume of the tumors is the lowest when mice were treated with paclitaxel followed by the administration of 19b.

Xenograft establishment and chemotherapy. For xenograft studies, 4-6 week old female nu/nu mice (Charles River Laboratories, Wilmington, Mass.) were anesthetized by intraperitoneal injection of ketamine (80 mg/kg) and xylazine (10 mg/kg) according to the protocol approved by the University of Utah Institutional Animal Care and Use Committee (IACUC). Before inoculation, MDA-MB-231 cells were trypsinized and resuspended in Extracel™ (Glycosan Bio-Systems, Salt Lake City, Utah) with a final concentration of $5 \times 10^7$ cells/mL, and the resulting suspension was mixed gently by vortexing. An aliquot of 200 μL of the mixture was injected subcutaneously into the fourth mammary fat pad of each mouse. The mice were randomly divided into various treatment groups and control groups (six mice per group). The treatment groups received i.p. injections of Taxol (10 mg/kg), BrP-LPA 1 (10 mg/kg), or Taxol (10 mg/kg) followed by BrP-LPA 1 (10 mg/kg). The control group was injected with physiological saline i.p. Injections were performed twice per week for two weeks starting at two weeks after the cell transplantation. The tumor sizes were measured and calculated by formula: tumor size $(mm^3)=[width\ (mm)]^2 \times [length\ (mm)]/2$. The mice were sacrificed at the end of the experiments, and the tumor tissue was removed for histogical H&E and immunohistochemistry using an anti-CD31 antibody. CD31 in zinc-fixed paraffin sections was detected using anti-rat Ig horseradish peroxidase (HRP) detection kit (BD Bioscience) following the manufacturer's instruction. Microvessels were counted at ×400 magnification, and the data converted to microvessel density (vessels/mm²) using equation, with 1 microscopic field=0.196 mm². Six fields were randomly chosen for quantification in three slides for each treatment group tumor tissue.

The effect of syn-BrP-LPA 1a and anti-BrP-LPA 1b were evaluated in a separate study following an analogous protocol. In this case, the Taxol treatment and Taxol/LPA analogue treatment were omitted. Moreover, an injection volume of 100 μL and a lower dosage of 3 mg/kg for 1a and for 1b were used.

Figure 9:
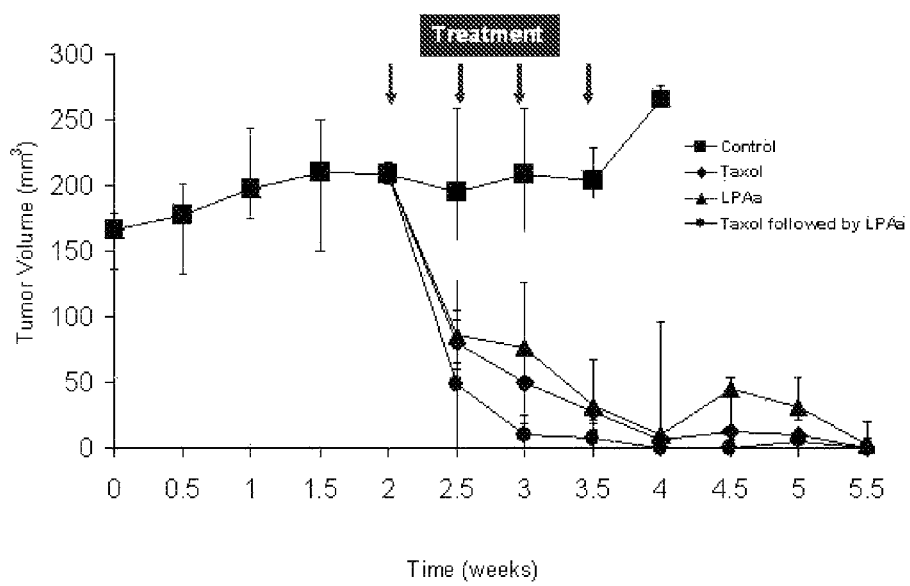
FIG. 9 shows that treatment of mice by intraperitoneal injection of the α-bromo
Figure 9:
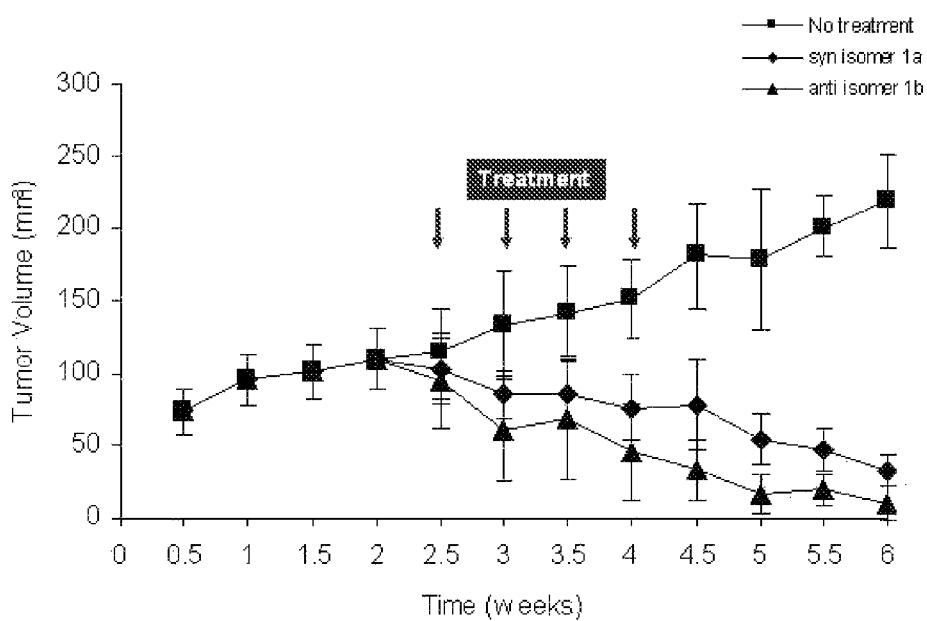

To evaluate the effects of BrP-LPA in vivo, "tumor engineering" was used to create orthotopic breast tumors in nude mice. FIG. 9a shows the effect of BrP-LPA 1 treatment on MDA-MB-231 tumor growth in vivo. FIG. 9b shows the effect of syn-BrP-LPA 1a and anti-BrP-LPA 1b treatment on MDA-MB-231 tumor growth in vivo. In the first experiment, the effects of the BrP-LPA 1 alone was compared with Taxol alone (FIG. 9a). A dual-drug therapy approach was also simulated by administering Taxol followed by the mixed diastereomers 1. Thus, subcutaneous mammary fat pad injection of MDA-MB-231 cells suspended in a semi-synthetic extracellular matrix analog (Extracel) in nu/nu mice resulted in tumor growth at all sites of injection. FIG. 9 shows the increase in tumor volumes during the growth phase, and decrease in tumor volumes during the treatment phase. After two weeks of tumor growth, the control group was treated with four intraperitoneal injections of physiological saline over the course of 2 weeks. The first treatment group received intraperitoneal injections of Taxol (10 mg/kg) and the second treatment group received intraperitoneal injections of BrP-LPA 1 (10 mg/kg), twice per week for two weeks. The third treatment group received two injections of Taxol (10 mg/kg) for week one, and two injections of BrP-LPA 1 (10 mg/kg) for the second week. In all three of the treatment groups, a reduction of tumor size was observed shortly after the first therapeutic injection, as compared to the control group (FIG. 9a).

After completion of the 2-week treatment course, tumors in all three treatment groups were significantly decreased or undetectable. At the end of the experiment, tumors were surgically removed and prepared for histology analysis. The largest tumor sample in the treatment group with diastereomer mixture 1 (FIG. 10a) was significantly smaller than the smallest tumor tissue in the control group (FIG. 10b), and the surface of the treatment tumor was very rough. H&E staining revealed an irregular arrangement of tumor cells and inflammatory granuloma tissue and an increased number of blood vessels (FIG. 10c) in the control group. An endothelial layer covering tumor vasculature was observed using immunohistochemical staining with anti-CD31 antibody (FIG. 10d). Quantification of the newly generated vessels in the tumor samples in six different fields of three slides for each treatment group (FIG. 10e) showed highly significant reduction of angiogenesis in the mice treated with the LPA antagonist mixture 1 relative to either controls or Taxol treatments ($p<0.01$).

To further examine the separate effects of the two diastereomers, syn-BrP-LPA 1a and anti-BrP-LPA 1b, a second xenograft study was performed using analogous protocols, except that the size of the injected cell suspension was reduced to 100 μL and the treatment dosage was reduced to 3 mg/kg. FIG. 14b shows that each isomer significantly decreased the tumor volume relative to the control group ($p<0.01$), with anti-BrP-LPA 1b exhibiting a trend towards higher efficacy relative to syn-BrP-LPA 1a ($p<0.1$).

Effects of bromo-LPA analogs on HCT 116 proliferation. HCT 116 cells were purchased from the American Type Culture Collection (Manassas, Mass.). Medium and reagents were obtained from the following sources: McCoy's 5a Medium (ATCC, Manassas, Va.); Penicillin-Streptomycin (MP biomedicals, Solon, Ohio); Fetal bovine serum (ATCC, Manassas, Mass.); Accutase (MP biomedicals, Solon, Ohio); MTS (Promega, Madison, Wis.); Matrigel (Becton Dickinson Labware, Cambridge, Mass.); Extracel (Glycosan, Salt Lake City, Utah). Lysophosphatidic acid receptor pan-Antagonist (LPAa)—the pure diastereomers 1a and 1b, and the mixed diastereomers 1 (University of Utah, Salt Lake City, Utah).

HCT 116 cells were maintained in McCoy's 5a medium supplemented with 10% FBS, 100 μg/ml streptomycin, and 100 units/ml penicillin at 37° C. in 95% air, 5% $CO_2$. 4,000 HCT-116 cells were seeded in 100 μl media in each well of 96-well flat-bottomed microplates (BD Labware, N.J.). The pure diastereomers 1a and 1b, and the mixed diastereomers 1 were added at various final concentrations (2 μM, 10 μM, 20 μM) to each column. At 72 h, pipet 20 μl MTS (Promega, Madison, Wis.) into each well, and cells were further incubated for 2 h. The absorbance of the samples at 490 nm was measured using a 96-well plate reader (OPTI max, Sunnyvale, Calif.).

Among the three LPAa, the pure BrP-LPA diastereomer 1b highly suppressed the proliferation of HCT 116 cells at a concentration of 20 μM compared to the pure diastereomer 1a and the mixed diastereomers 1. Treatment of the pure diastereomers 1b with HCT 116 caused a dose-dependent inhibition in tumor cell proliferation (FIG. 11). The greatest inhibition was observed in HCT 116 colon cancer cells at 20 µM of the pure diastereomer 1b.

Effects of BrP-LPA analogs on HCT 116 invasion. The effect of LPAa on HCT-116 cells was determined by 24-well Transwell® permeable support (Corning, Lowell, Mass.) and basement membrane Matrigel (Becton Dickinson Labware, Cambridge, Mass.) invasion assay. The 8 µm pore polycarbonate filters were coated with basement membrane Matrigel (50 µg/filter).

HCT 116 cell suspensions in culture medium containing $5\times10^4$ cells/ml were prepared. To the suspensions, 0.75 ml medium containing various concentrations of the pure diastereomers 1a and 1b, and the mixed diastereomers 1 (2 µM, 10 µM, 20 µM) were added to each well of the BD plate. Sterile forceps were used to transfer the support inserts and control inserts to the wells containing LPAa. 0.5 ml of HCT 116 cell suspension ($2.5\times10^4$ cells) was immediately added to the inserts. The Matrigel invasion inserts were incubated for 22 hours at 37° C., 5% $CO_2$ incubator. The non-invading cells and Matrigel were gently removed from the upper membrane surface using a cotton-tipped swab. The cells on the lower surface of the membrane were stained with Diff-Quik (IMEB Inc., San Marcos, Calif.). Cells were examined under a light microscope. Under ×100 magnification, five randomly selected fields in each chamber were examined, each group having 6 inserts, and the mean number or cells invaded was calculated. Invasion was expressed as the percent invasion for each LPAa concentration through the Matrigel matrix and membrane relative to the migration through the control membrane. The results of these experiments (FIG. 12) show that all three bromo-analogs inhibit the invasive capacity of HCT 116 cells in a dose-dependent manner.

Effects of BrP-LPA analogs on HCT 116 migration. HCT 116 ($2\times10^5$ per well) were plated in a six-well plate. When the cells were 100% confluent, the cells were treated with Mitomycin C (Sigma, MO, USA) 10 µg/ml for 2 hours, and then the monolayer was scratched using a 200 µl pipette tip. Medium and nonadherent cells were aspirated, the adherent cells were washed once, and new medium containing various concentrations of the pure diastereomers 1a and 1b, and the mixed diastereomers 1 (2 µM, 10 µM, 20 µM) was added (FIG. 13). A photograph was taken at the marked field (n=4) at 0, 16, 24 and 48 hours (FIG. 14). Wound closure was expressed as a percentage of the initial wound area, which was quantified using NIH ImageJ software.

The pure diastereomer 1b at 20 µM concentration showed the greatest inhibition of colon cancer cell migration in every time point (FIG. 14) (data of the pure diastereomers 1a and the mixed diastereomers 1 not shown).

Effect of BrP-LPA analogs on hepatic tumor growth. The experimental protocol and animal care complied with the "Guide for the Care and Use of Laboratory Animals" (Institute of Laboratory Animal Resources, Commission on Life Sciences, National Research Council, Washington, D.C.; National Academy Press, 1996), and were approved by the Institutional Animal Care and Use Committee of the University of Utah.

Four-week-old female athymic nude mice (Charles River Laboratories, Wilmington, Mass.) were used for colon cell implantation. All animals were maintained in a sterile environment. Cages, bedding, food, and water were all autoclaved. All animals were maintained on a daily 12-hr light/12-hr dark cycle.

Nude mice were anesthetized by intraperitoneal injection of ketamine (80 mg/kg) and xylazine (10 mg/kg) according to the protocol approved by the University of Utah Institutional Animal Care and Use Committee (IACUC).

After anesthesia induction, the aseptic surgical field was sterilized with iodine and alcohol swabs. HCT 116 cells ($1\times10^6$) in 50 µl of the sECM hydrogel Extracel was directly injected into the livers of nude mice after they had been randomly assigned to one of the groups at the beginning of the experiment (8 mice/group).

The control group received physiological saline i.p. injection twice per week starting at one week after the cell transplantation and ended at two weeks after the treatment. The treatment group received i.p. administration of the pure diastereomers 1b at 10 mg/kg twice per week with the same period of control group.

Mice were observed daily. Animals were euthanized at 3 weeks post-injection in a carbon dioxide chamber. Body weights were measured, and the livers were excised. Liver weights and tumor diameters were subsequently determined. Colon tumors were measured using digital calipers. The volume of the cancer was then calculated according to the formula: Cancer Volume (CV)=$d^2 \times D/2$, where d and D are the shortest and the longest diameters, respectively. After measurement, the tumor tissue was then harvested and placed in 10% formalin for paraffin embedding in preparation for the subsequent histological analyses.

All nude mice in both groups developed liver tumors. Autopsies showed the implanted HCT 116 formed tumors grew extensively in liver area in the untreated group. The tumor in the group treated with 1b was significantly smaller than the control. The hepatic colon tumor in the control group averaged approximately 14.5×19.0 mm and 7.2×10.0 mm in the treated group. No local or distal organ metastasis was observed. Representative photographs of excised liver are presented in FIG. 15. The group treated with 1b showed a marked reduction of hepatic tumor burden (liver weight; p<0.05; FIG. 21a). LPAa treatment also led to a significant decrease in tumor volume (p<0.05; FIG. 16b).

H&E staining illustrates the distinct interface between hepatic colon cancer and mouse native liver. FIG. 17b shows the pathohistology of the tumor-involved nude mouse liver as shown in FIG. 17a. The upper section in FIG. 17b (1) shows hepatic colon cancer growth on nude mouse. The lower section (2) shows the native nude mouse liver (100×). The arrangement of cell in cancer section was irregular. FIG. 17c shows H&E staining of untreated colon cancer cells, where newly generated blood vessels were observed. Conversely, colon cancer cells treated with 1b showed significantly reduced amounts of new blood vessels (FIG. 17d), which indicates that the BrP-LPA analog 1b can inhibit tumor angiogenesis.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

TABLE 1

Effects of methylene phosphonate analogs at LPA GPCRs and PPARγ-PPRE luciferase reporter gene assay

| Compd. | LPA$_1$ EC$_{50}$ (E$_{max}$)[b] nM | LPA$_1$ IC$_{50}$ (K$_i$) nM | LPA$_2$ EC$_{50}$ (E$_{max}$) nM | LPA$_2$ IC$_{50}$ (K$_i$) nM | LPA$_3$ EC$_{50}$ (E$_{max}$) nM | LPA$_3$ IC$_{50}$ (K$_i$) nM | LPA$_4$ EC$_{50}$ (E$_{max}$) nM | LPA$_4$ IC$_{50}$ (K$_i$) nM | PPARγ |
|---|---|---|---|---|---|---|---|---|---|
| LPA (18:1) | 100.2 ± 13.2 | NE | 4.21 ± 0.7 | NE | 150.2 ± 15.5 | NE | 256.1 ± 33.5 | NE | Agonist |
| LPA (16:0) | 90.8 ± 20.9 (88.7 ± 3.6) | NE | 55.1 ± 4.3 (100.3 ± 1.9) | NE | 1527 ± 194.2 (71.2 ± 2.9) | NE | 843.4 ± 130.1 (102.4 ± 4.1) | NE | NE |
| 20a | >2520 (52.9 ± 11.3) | NE[c] | >281 (94.7 ± 4.3) | NE | >1710 (63.5 ± 4.8) | NE | 3900 ± 104 (110 ± 1.3) | NE | NE |
| 20b | NE | PA[d] | NE | 2590 ± 875 (1296 ± 438) | NE | 2560 ± 1160 (961 ± 435) | 5400 ± 526 (29.3 ± 1.1) | NE | NE |
| 22a | >9250 (39.1 ± 3.15) | NE | >2160 (71.9 ± 6.0) | NE | 393 ± 89 (116 ± 9.5) | NE | >1150 (71.7 ± 2.0) | NE | NE |
| 22b | NE | PA[e] | NE | PA[f] | NE | PA[g] | NE | NE | NE |
| 18a | 528 ± 72 (63.2 ± 9.5) | NE | NE | 1690 ± 85 (845 ± 42.5) | >2670 (63.5 ± 3.7) | NE | 3480 ± 561 (40.5 ± 2.7) | NE | NE |
| 18b | NE | 2490 ± 690 (919 ± 255) | NE | 855 ± 113 (428 ± 56.5) | NE | 175 ± 190 (98.3 ± 105) | NE | PA[h] | NE |
| 19a | NE | 1620 ± 116 (694 ± 49.7) | NE | 815 ± 60 (174 ± 12.8) | >2470 (44.2 ± 3.5) | NE | NE | 4000 ± 424 (2500 ± 266) | NE |
| 19b | NE | 1500 ± 559 (751 ± 280) | NE | 1420 ± 83 (304 ± 17.7) | NE | 1160 ± 259 (380 ± 84.9) | NE | 266 ± 124 (167 ± 77.8) | NE |
| 24a | NE | PA[i] | NE | PA[j] | NE | PA[k] | NE[l] | | NT[m] |
| 24b | NE | PA[n] | NE | PA[o] | NE | PA[p] | NE[l] | | NT |

[a]Data represent the average of four independent measures (mean ± s.d.).
[b]E$_{max}$ = (maximal efficacy of compound/maximal efficacy of LPA 18:1) × 100.
[c]NE = no effect was shown at the highest concentration (30 μM) tested.
[d]PA = partial antagonist with 39.0 ± 3.2% inhibition of 200 nM LPA response at the highest concentration (30 μM) tested.
[e]PA = partial antagonist with 37.1 ± 6.8% inhibition of 200 nM LPA response at the highest concentration (30 μM) tested.
[f]PA = partial antagonist with 57.8 ± 4.9% inhibition of 10 nM LPA response at the highest concentration (30 μM) tested.
[g]PA = partial antagonist with 63.3 ± 3.7% inhibition of 200 nM LPA response at the highest concentration (30 μM) tested.
[h]PA = partial antagonist with 80.0 ± 11.2% inhibition of 400 nM LPA response at the highest concentration (30 μM) tested.
[i]PA = partial antagonist with 35.6 ± 9.7% inhibition of 200 nM LPA response at the highest concentration (30 μM) tested.
[j]PA = partial antagonist with 54.8 ± 6.1% inhibition of 10 nM LPA response at the highest concentration (30 μM) tested.
[k]PA = partial antagonist with 73.3 ± 7.5% inhibition of 200 nM LPA response at the highest concentration (30 μM) tested.
[l]NE alone, but increased LPA response when applied together with LPA
[m]NT = not tested
[n]PA = partial antagonist with 41.1 ± 5.4% inhibition of 200 nM LPA response at the highest concentration (30 μM) tested.
[o]PA = partial antagonist with 52.8 ± 8.5% inhibition of 10 nM LPA response at the highest concentration (30 μM) tested.
[p]PA = partial antagonist with 73.5 ± 8.0% inhibition of 200 nM LPA response at the highest concentration (30 μM) tested.

TABLE 2

Pharmacological results with 1, 1a, and 1b

| | LPA$_1$ | LPA$_2$ | LPA$_3$ | LPA$_4$ | LPA$_5$ | ATX |
|---|---|---|---|---|---|---|
| 1 | Antagonist IC$_{50}$: 4520 ± 1521 nM K$_i$: 805 nM | Antagonist IC$_{50}$: 468 ± 322 nM K$_i$: 245 nM | Partial Antagonist 71.3% Inhibition at 30 μM (200 nM LPA) | Partial Antagonist 13.9% Inhibition at 30 μM (400 nM LPA) | Partial Agonist EC$_{50}$: 1282 ± 222 nM E$_{max}$: 54% at 10 μM | 102 ± 2.7% Inhibition (10 μM) |
| 1a | Antagonist IC$_{50}$: 648 ± 475 nM K$_i$: 273 nM | Antagonist IC$_{50}$: 288 ± 103 nM K$_i$: 250 nM | Antagonist IC$_{50}$: 4440 ± 1850 nM K$_i$: 1830 nM | Partial Antagonist 35.1% Inhibition at 30 μM (400 nM LPA) | Partial Agonist NS[§] E$_{max}$: 64% at 10 μM | 98.1 ± 2.3% Inhibition (10 μM) |
| 1b | Antagonist IC$_{50}$: 2079 ± 1544 nM K$_i$: 752 nM | Antagonist IC$_{50}$: 275 ± 133 nM K$_i$: 241 nM | Antagonist IC$_{50}$: 2089 ± 1212 nM K$_i$: 623 nM | Partial Antagonist 33.1% Inhibition at 30 μM (400 nM LPA) | Antagonist IC$_{50}$: 977 ± 493 nM K$_i$: 376 nM | 99.4 ± 2.7% Inhibition (10 μM) |

[§]NS; non-saturated

TABLE 3

Inhibition of autotaxin (ATX) phosphodiesterase activity by LPA analogues

| Compound | Concentration (µM) | Inhibition (%) | Compound | Concentration (µM) | Inhibition (%) |
|---|---|---|---|---|---|
| LPA (18:1) | 10.0 | 88.4 ± 1.3 | 18a | 10.0 | 92.5 ± 2.1 |
| LPA (16:0) | 10.0 | 38.1 ± 3.4 | 18b | 10.0 | 83.0 ± 2.1 |
| 2ccPA (16:1) | 10.0 | 78.5 ± 2.3 | 19a | 10.0 | 90.7 ± 2.3 |
| 20a | 10.0 | 99.8 ± 2.3 | 19b | 10.0 | 93.7 ± 2.0 |
| 20b | 10.0 | 60.6 ± 4.6 | 24a | 10.0 | 56.6 ± 6.0 |
| 22a | 10.0 | 74.7 ± 4.3 | 24b | 10.0 | 43.4 ± 6.0 |
| 22b | 10.0 | 54.1 ± 5.7 | | | |

What is claimed:

1. A compound having the formula I

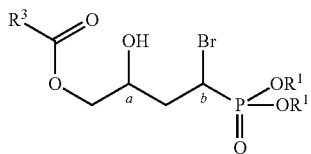

wherein
each $R^1$ is, independently, hydrogen, a branched or straight chain $C_1$ to $C_{25}$ alkyl group, a cationic counterion, or both $R^1$ form a cyclic or heterocyclic group; $R^3$ is a branched or straight chain $C_1$ to $C_{25}$ alkyl group, a cycloalkyl group, a heterocycloalkyl group, an aryl group, a heteroaryl group,
or the pharmaceutically acceptable salt or ester thereof, wherein the stereochemistry at carbon a is substantially S, and the stereochemistry at carbon b is substantially R or substantially S.

2. The compound of claim 1, wherein $R^3$ is a branched or straight chain $C_1$ to $C_{25}$ alkyl group, and each $R^1$ is hydrogen.

3. The compound of claim 2, wherein $R^3$ is an oleate group or a palmitate group.

4. The compound of claim 1, wherein the stereochemistry at carbon b is substantially R.

5. The compound of claim 1, wherein the stereochemistry at carbon b is substantially S.

6. The compound of claim 1, wherein the compound is 1-(S)-bromo-3-(S)-hydroxy-4-(palmitoyloxy)butyl]phosphonate.

7. The compound of claim 1, wherein the compound is 1-(R)-bromo-3-(S)-hydroxy-4-(palmitoyloxy)butyl]phosphonate.

8. A pharmaceutical composition comprising a pharmaceutically-acceptable compound and the compound of claim 1.

9. The compound of claim 1, wherein the stereochemistry at carbon a is greater than 95% the S enantiomer with respect to the R enantiomer.

10. The compound of claim 9, wherein the stereochemistry at carbon b is greater than 95% the S enantiomer with respect to the R enantiomer.

11. The compound of claim 9, wherein the stereochemistry at carbon b is greater than 95% the R enantiomer with respect to the S enantiomer.

\* \* \* \* \*